US011077119B2

(12) United States Patent
Maelicke

(10) Patent No.: US 11,077,119 B2
(45) Date of Patent: Aug. 3, 2021

(54) ENHANCED BRAIN BIOAVAILABILITY OF GALANTAMINE BY SELECTED FORMULATIONS AND TRANSMUCOSAL ADMINISTRATION OF LIPOPHILIC PRODRUGS

(71) Applicant: Neurodyn Life Sciences Inc., Charlottetown (CA)

(72) Inventor: Alfred Maelicke, Nieder-Olm (DE)

(73) Assignee: Neurodyn Life Sciences Inc., Charlottetown (CA)

( * ) Notice: Subject to any disclaimer, the term of this patent is extended or adjusted under 35 U.S.C. 154(b) by 9 days.

(21) Appl. No.: 16/287,413

(22) Filed: Feb. 27, 2019

(65) Prior Publication Data

US 2019/0262352 A1 Aug. 29, 2019

Related U.S. Application Data

(63) Continuation of application No. 14/417,502, filed as application No. PCT/EP2013/065880 on Jul. 29, 2013, now abandoned.

(60) Provisional application No. 61/676,348, filed on Jul. 27, 2012.

(30) Foreign Application Priority Data

Jul. 27, 2012 (EP) .................................. 12178187

(51) Int. Cl.
| | | |
|---|---|---|
| *A61K 31/55* | (2006.01) | |
| *A61K 9/14* | (2006.01) | |
| *A61K 31/00* | (2006.01) | |
| *A61K 9/20* | (2006.01) | |
| *A61K 9/28* | (2006.01) | |
| *A61K 9/107* | (2006.01) | |
| *A61K 9/00* | (2006.01) | |

(52) U.S. Cl.
CPC .............. *A61K 31/55* (2013.01); *A61K 9/006* (2013.01); *A61K 9/0043* (2013.01); *A61K 9/1075* (2013.01); *A61K 9/14* (2013.01); *A61K 9/2072* (2013.01); *A61K 9/2086* (2013.01); *A61K 9/2846* (2013.01); *A61K 9/2886* (2013.01); *A61K 31/00* (2013.01); *Y02A 50/30* (2018.01)

(58) Field of Classification Search
None
See application file for complete search history.

(56) References Cited

U.S. PATENT DOCUMENTS 5,073,374 A * 12/1991 McCarty .............. A61K 9/0056
424/434
5,250,287 A 10/1993 Cocozza 2003/0235617 A1 * 12/2003 Martino ................ A61K 9/0056
424/481
2004/0254146 A1 12/2004 Quay et al.
2005/0065176 A1 3/2005 Field et al.
2008/0269310 A1 * 10/2008 Foster .................. A61K 31/195
514/411
2008/0305077 A1 12/2008 Frey, II et al.
2009/0253654 A1 10/2009 Maelicke et al.
2013/0317117 A1 11/2013 Hassan

FOREIGN PATENT DOCUMENTS

| JP | 2005-507411 A | 3/2005 |
| JP | 2007-534686 A | 11/2007 |
| WO | WO 03/037329 A1 | 5/2003 |
| WO | WO 2005/102275 A2 | 11/2005 |
| WO | WO 2007/039138 A1 | 4/2007 |
| WO | WO 2009/127218 A1 | 10/2009 |

OTHER PUBLICATIONS

Buttini et al. 2012 "Particles and powders: Tools of innovation for non-invasive drug administration" *Journal of Controlled Release* 161: 593-702.

(Continued)

*Primary Examiner* — David J Blanchard
*Assistant Examiner* — Sarah J Chickos
(74) *Attorney, Agent, or Firm* — Knobbe, Martens, Olson & Bear, LLP

(57) ABSTRACT

A method of treating a subject for a brain disease associated with cognitive impairment, including administering to a subject a chemical substance according to GLN-1062 or salt thereof:

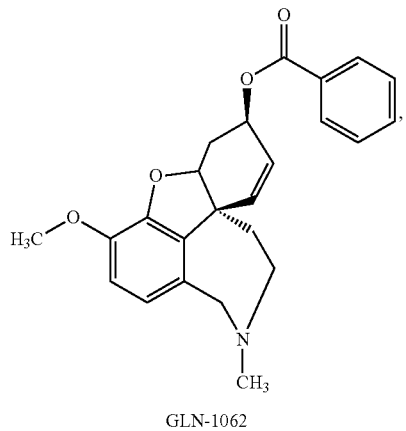

Figure 1:
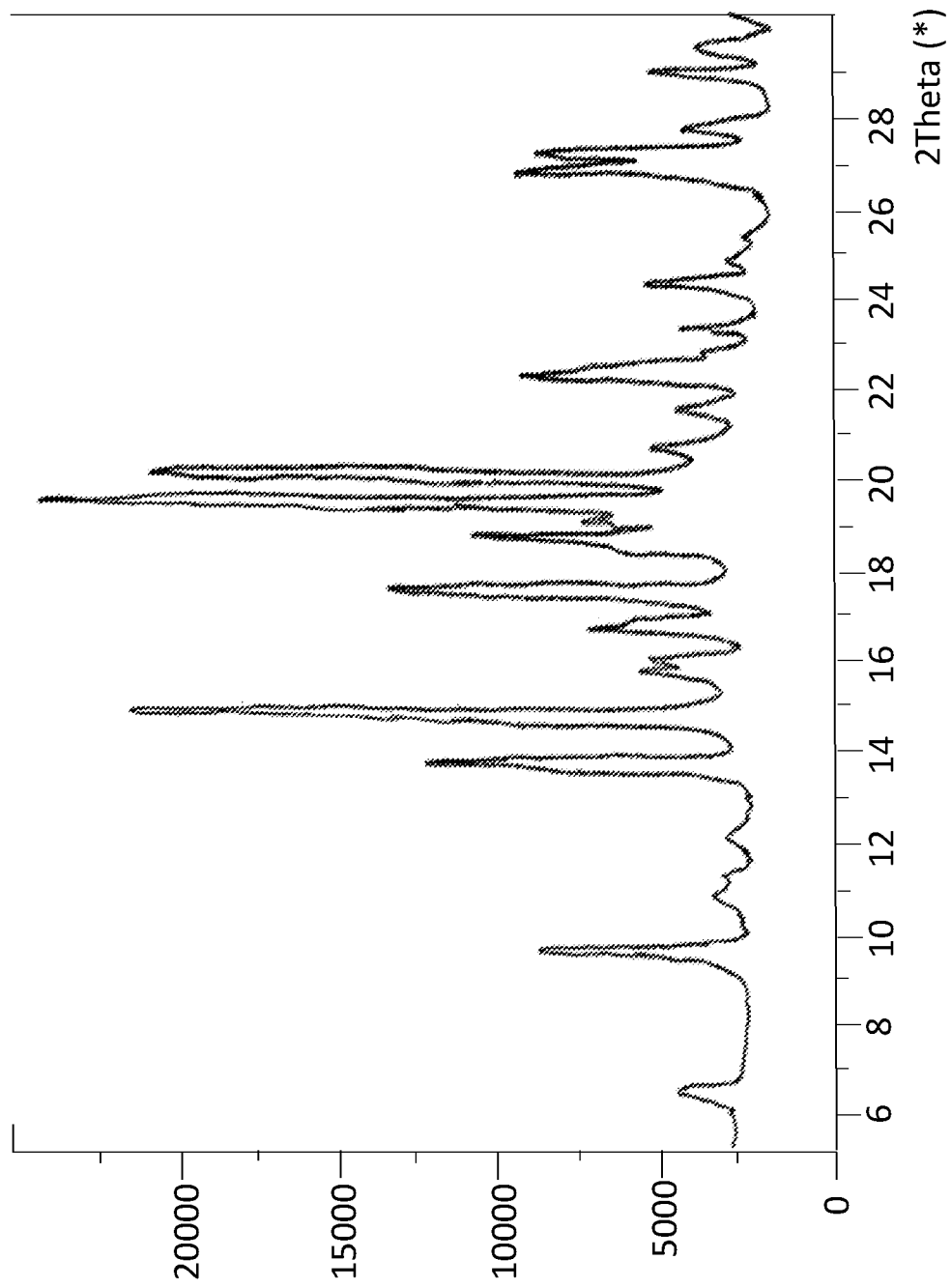

GLN-1062 wherein the treatment includes transmucosal administration of a therapeutically effective amount of GLN 1062 or salt thereof in the oral cavity of the subject.

13 Claims, 10 Drawing Sheets

(56) References Cited

OTHER PUBLICATIONS

De Caro, V. et al. 2008 "Evaluation of galantamine transbuccal absorption by reconstituted human oral epithelium and porcine tissue as buccal mucosa models: Part I" *European Journal of Pharmaceutics and Biopharmaceutics* 70(3): 869-873.
Kaletta, T. et al. 2010 "Memogain, a novel high potency drug treatment for AD" *Society for Neuroscience Abstract, Program/Poster #* 748.23/G26, presented Wednesday Nov. 17, 2010, (in 2 pages).
Leonard, A.K. et al. 2007 "In vitro formulation optimization of intranasal galantamine leading to enhanced bioavailability and reduced emetic response in vivo" *International Journal of Pharmaceutics* 335(1-2): 138-139.
Maelicke, A. et al. 2010 "Memogain is a galantamine pro-drug having dramatically reduced adverse effects and enhanced efficacy" *Journal of Molecular Neuroscience* 40(1-2): 135-137.
Shen, Ying, "Studies on insulin self-microemulsifying drug delivery systems for intranasal administration" Theses Full text Database (Master) Medicine and Health Sciences, E079-21, Abstract, published Dec. 15, 2005.
Tirucherai et al. 2001 "Prodrugs in nasal delivery" *Exper Opin Biol Ther* 1(1): 49-66.
Wong et al. et al. 2010 "Intranasal Delivery—Modification of drug metabolism and brain disposition" *Pharm Res* 27: 1208-1223.
Yajima et al. 1998 "Direct transport of 2'3'-Didehydro-3'-deoxythymidine (D4T) and its ester derivatives to the cerebrospinal fluid via the nasal mucous membrane in rats" *Biol Pharm Bull* 21(3): 272-277.
Zhang, Qiang et al., "Quality control of aerosols" in *Pharmaceutical Textbook of Peking University (Pharmaceutics)* Peking University Medical Press, pp. 255-257, published Jan. 31, 2005.
Chen, Yongfa, "Part II Guidelines for Drug Registration—Writing format and content of technical guidelines for inhalation preparation quality control research," Guidelines for Drug Registration, published Sep. 1, 2011, p. 199.
Modern Pharmaceutical Preparation Technology Series, vol. 2, published by Peking University, School of Medicine. Chapter Two, Drug Solubility, pp. 117-118. May 1976.
Shen, Yin "Studies on Insulin Self-Microemulsifying Drug Delivery System for Intranasal Administration (Abstract)," Chinese Doctoral Dissertations & Master's Theses Full-text Database (Master, Medicine and Health Sciences, 2005, vol. 8, Published between Nov. 16, 2005-Dec. 15, 2005.
Dodou, K. (2012 "Research and developments in buccal and sublingual drug delivery systems" The Pharmaceutical Journal, downloaded from the World-Wide Web at: pharmaceutical-journal.com/news-and-analysis/research-and-developments-in-buccal-and-sublingual-drug-delivery-systems/11098641.article?firstPass=false.
Darwish 2011 "Pharmacokinetics of Fentanyl Buccal Tablet: A Pooled Analysis and Review" Pain Practice, vol. 12, Issue 4, 2012 307-314.
Ryden et al. (1987 "Buccal Versus Sublingual Nitroglycerin Administration in the Treatment of Angina Pectoris: A Multicentre Study" Eur Heart J. 8(9): 995-1001.

\* cited by examiner

ENHANCED BRAIN BIOAVAILABILITY OF GALANTAMINE BY SELECTED FORMULATIONS AND TRANSMUCOSAL ADMINISTRATION OF LIPOPHILIC PRODRUGS

The invention relates to selected administration routes for CNS (central nervous system) therapeutics and highly soluble salts, solutions, emulsions or powder formulations thereof, having optimal brain delivery due to the mode of administration and the chemical nature of the compounds of the invention. The therapeutic compounds of the present invention relate to lipophilic pro-drugs of pharmacologically active compounds that—as prodrugs—are inactive in regard to their major targets in the CNS, in particular cholinesterases and/or nicotinic acetylcholine receptors. Via cleavage by endogenous enzymes, the pharmacologically active parent drugs are produced and act as allosterically potentiating ligands (APL) on nicotinic acetylcholine receptors (nAChR), and/or as reversible inhibitors of acetylcholinesterases (AChE) and other cholinesterases (ChE). To maximize transport through the blood-brain barrier (BBB) and in order to protect the prodrugs of the invention from cleavage by endogenous esterases before crossing the BBB to their site(s) of action, the pro-drugs are designed to be highly lipophilic (log P>2.5) and are delivered via transmucosal absorption pathways in the oral or nasal cavity.

BACKGROUND OF THE INVENTION

Currently, the first line of drug treatment for Alzheimer's disease (AD) is the use of cholinesterase inhibitors, such as donepezil, rivastigmine and galantamine. Among these, galantamine has been shown to have a distinct second mode of action, i.e. allosterical sensitisation of nicotinic acetylcholine receptors (Maelicke A; Albuquerque E X (1996) New appoaches to drug therapy in Alzheimer's dementia. Drug Discovery Today 1, 53-59). Galantamine enhances the probability of channel opening induced by submaximal concentrations of acetylcholine (ACh), or choline (Ch), or other nAChR agonists. Because progression of AD is associated by an increasing loss of nAChR, the APL-enhanced activity of nicotinic receptors is a suitable symptomatic and possibly also disease-modifying treatment for AD and other forms of dementia (Storch A et al. (1995). Physostigmine, galantamine and codeine act as noncompetitive nicotinic agonists on clonal rat pheochromocytoma cells. Eur J Biochem 290: 207-219; Kihara T et al. (2004) Galantamine modulates nicotinic receptors and blocks A1-enhanced glutamate toxicity. Biochem Biophys Res Commun 325: 976-982; Akata K et al. (2011) Galantamine-induced amyloid-clearance mediated via stimulation of microglial nicotinic acetylcholine receptors. J Biol Chem 286; Maelicke A (2006) Allosteric sensitisation of brain nicotinic receptors as a treatment strategy in Alzheimer's dementia. In: Therapeutic Strategies in Dementia (Eds: Ritchie C W, Ames D J, Masters C L, Cummings J), Clinical Publishing, Oxford, 2006; 153-172)).

In contrast to rivastigmine and donepezil, galantamine does not significantly enrich in the human brain in comparison to blood plasma. This is because galantamine, being a plant alkaloid rather than a rationally designed drug, is much less lipophilic than the other two cholinesterase inhibitors used as drugs in AD and hence exhibits in steady-state only a rather low brain-to-blood concentration ratio (BBCR<2).

To enhance the lipophilicity of CNS drugs and their passage through the blood-brain barrier, hydrophobic side chains have been appended to the basic alkaloid structures, as described in EP1 940 817 B1 and WO 2009/127218 A1. The attached groups were selected in order to increase the BBRC to larger than 5.

Similar to other cholinesterase inhibitors, galantamine has a clinically significant level of mechanism-based gastrointestinal (GI) side effects, including nausea, vomiting and diarrhea (Loy C et al., Galantamine for Alzheimer's disease and mild cognitive impairment. Cochrane Database of Systematic Reviews 2006, Issue 1). To accommodate patients to these side effects, cholinesterase inhibitors usually are initially administered at a low (non-efficacious) dose, with the dose being carefully up-titrated to an efficacious one, within a period of months. Moreover, the maintenance dose often is adjusted to what the patients experience as an acceptable level of GI side effects, making it likely that most, if not all, patients never achieve treatment with the most effective dose. Accordingly, cholinesterase inhibitors are generally perceived as of only low effectiveness and as associated with unpleasant side effects. In light of the prior art regarding the administration of galantamine, it becomes apparent that the potential therapeutic efficacy of galantamine has never been able to be applied in human subjects to its full extent due to the poor brain-to-blood concentration ratio and significant peripheral side effects arising from poor brain delivery.

Because galantamine is known to affect motor and evacuative function of intestinal tissue (Turiiski V I et al. (2004), in vivo and in vitro study of the influence of the anticholinesterase drug galantamine on motor and evacuative functions of rat gastrointestinal tract. Eur J Pharmacol 498, 233-239), a reduction in GI side effects of galantamine was attempted by intranasal rather than oral administration of the drug (Leonard A K et al. (2007), In vitro formulation optimization of intranasal galantamine leading to enhanced bioavailability and reduced emetic response in vivo. Int J Pharmaceut 335: 138-146).

Because of the limited volume of spray that can be applied in one spray event to each nostril, the intranasal route of administration requires highly soluble drug product formulations. This was only in part achieved for galantamine by replacing in the hydrobromide of the drug the bromide ion by lactate or gluconate. This change in salt form did not significantly improve transport through the BBB of galantamine, as it is the rather hydrophilic and polar galantamine base that is resorbed at the nasal epithelium and then transported across the blood-brain barrier. Because of these physicochemical limitations, galantamine and its tertiary and quarternary nitrogen salts exhibit brain-to-blood concentration ratios below 2, meaning that such drugs must be administered in rather large quantities in order to achieve significant drug levels in the target organ brain. Sufficiently effective doses in the brain of such hydrophilic drugs are therefore achieved at the expense of considerable levels of peripheral side effects, in particular gastro-intestinal side effects. It can be concluded that salt formulations of galantamine have not provided a satisfactory solution for enhancing the brain drug distribution via the BBB.

As described previously (WO2009/127218 A1), the relatively hydrophilic parent drugs of interest can be reformulated by chemical conversion to lipophilic ester pro-drugs. Alcoholic OH groups have been used for attaching aliphatic, aromatic or heteroaromatic carboxylic acids to the parent drug thereby (i) partially or fully inactivating them pharmacologically, and (ii) significantly enhancing their lipophilicity and BBB penetration.

Although ester formation is a commonly employed approach to increase the lipophilicity of polar molecules having limited BBB penetration, the abundance of nonspecific esterases in brain and peripheral tissues limits the effectiveness of this approach in enhancing brain/plasma concentration ratios of drugs. To maximize brain drug levels by the pro-drug approach, the kinetics of absorption, BBB penetration and bioconversion of pro-drug to drug in the target organ brain have to be sufficiently fast in order to successfully compete with elimination from brain of the less lipophilic drug after its generation. There remain therefore significant hurdles in the development of strategies, methods and/or medicinal agents that allow or exhibit reliable penetration of the BBB and are cleaved in the target organ (brain), in order to provide an enhanced amount of active substance in the brain without leading to cleavage in other organs or tissues of the body, which leads in many cases to substantial side-effects during treatment.

The possibility of intranasal administration of galantamine derivatives is disclosed in US 2009/0253654 A1. No mention is made of enhanced delivery to the brain or of means of avoiding in vivo enzymatic cleavage by endogenous esterases of the ester prodrug compounds post-administration. The salts and concentrations of the compounds disclosed in US 2009/0253654 A1 represent arbitrary disclosures without regard to the in vivo properties of the compounds. Neither specific salts nor transmucosal administration routes are disclosed with respect to GLN 1062.

WO2009/127218 A1 and Maelicke et al (J Mol Neurosci, 2010, 40:135-137) disclose GLN 1062 as such and its administration in the treatment of brain disorders with cognitive deficit. No mention is made of particular modes of administration or of particular salts. These earlier disclosures are based on intravenous administration of the compounds disclosed therein. Such bolus injections permit very fast distribution from blood to other organs, including the brain, and hence reduce the probability of enzymatic cleavage prior to reaching the BBB and distribution to the brain. Intravenous administration is however not acceptable for daily patient self-administration. More easily administered but equally effective alternatives are required.

Leonard A K et al. (2007, Int J Pharmaceut 335: 138-146) discloses intranasal administration of the lactate salt of galantamine. No particular effect is prescribed to the use of the lactate salt. The polar galantamine base is resorbed at the nasal epithelium and then transported across the blood-brain barrier, but only poorly, according to its limited propensity for brain drug distribution via the BBB. US 2004/0254146 discloses various salts of galantamine including lactate and gluconate salts and their administration in Alzheimer's disease. Neither US 2004/0254146 nor Leonard A K et al. is relevant for administration of salts of GLN 1062, which—due to its prodrug properties—represents the solution to an entirely different technical problem when compared to galantamine.

SUMMARY OF THE INVENTION

Transmucosal routes of delivery for the compounds described herein in the oral and nasal cavity have been examined as non-invasive routes of pro-drug administration best suited to achieve enhanced levels of drug in the brain. For systemic drug delivery, transmucosal routes are enhanced by prodrug salt formulations that accommodate to the structure and environment of the particular absorption area.

The advantageous transport properties of the pro-drugs discussed herein can be achieved when the pro-drugs are administered by intravenous injections, but less well, or only to a very small extent, when they are administered orally as tablets. This is because the pro-drugs are esters that have now been found to be instable in acidic environment (such as exists in the stomach) and are also cleaved enzymatically in many tissues, including in the intestines and in the liver (first-pass effect). In light of these findings and the problems of the administration methods of the prior art, and in order to take advantage of the nature of the pro-drugs in the treatment of CNS diseases, the invention makes use of administration routes that avoid the gastro-intestinal tract and the first-pass effect. These routes provide brain delivery about as efficiently as intravenous injection, which due to significant medical risk is normally not suited for reliable self-administration. The invention provides special pharmaceutical formulations to be used for the selected routes of administration that optimize rapid resorption and uptake of prodrug into the brain.

In light of the prior art the technical problem underlying the present invention is to provide alternative or improved means for enhanced bioavailability of the CNS therapeutics described herein, thereby providing effective treatment of brain diseases associated with cognitive impairment.

This problem is solved by the features of the independent claims. Preferred embodiments of the present invention are provided by the dependent claims.

Therefore, an object of the invention is to provide a chemical substance according to Formula I for use as a medicament in the treatment of brain disease associated with cognitive impairment, wherein said treatment comprises transmucosal administration, selected from intranasal, sublingual or buccal administration, of a therapeutically effective amount of said substance,

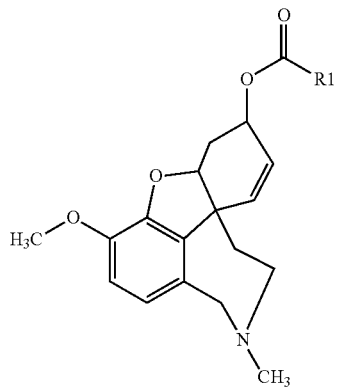

Formula I wherein
R1=aromatic or heteroaromatic 5- or 6-membered ring, such as optionally substituted benzene, naphthaline, thiophene, pyrrole, imidazole, pyrazole, oxazole, thiazole; or straight or branched chained aliphatic residues, such as $CH(C_2H_5)CH_3$, $CH_2$—$C(CH_3)_3$, cyclopropane or preferably an aliphatic residue comprising more than 5 C atoms, more preferably 6 C atoms, or more than 10 C atoms, such as a fatty acid residue.

The invention relates therefore primarily to the use of, or a method of treatment comprising administration of, the chemical substance as described herein for the treatment of brain disease associated with cognitive impairment by administering a therapeutically effective amount of said chemical substance by a transmucosal route selected from intranasal, buccal and/or sublingual administration.

In a preferred embodiment the chemical substance of the present invention is characterised in that the substance is selected from Formula II,

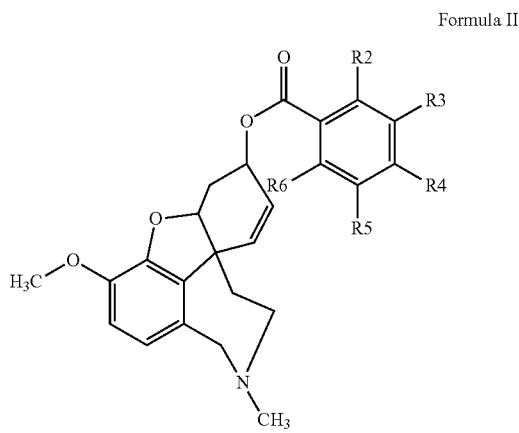

Formula II wherein

R2-R6 comprise of any substituent selected from H, halogen, optionally substituted $C_1$-$C_3$ alkyl or cyclopropyl, OH, O-alkyl, SH, S-alkyl, $NH_2$, NH-alkyl, N-dialkyl, optionally substituted aryl or heteroaryl, whereby neighbouring substitutents can cooperate to form an additional ring.

The optional substitution of the substituents described in Formula I and II relates to substitution with an alkyl, OH, halogen, $NH_2$, alkyl-$NH_2$ or $NO_2$ group, or other substituent described with regard to those compounds provided Table 2.

Compounds according to Formula I or II with aromatic or heteroaromatic 5- or 6-member rings at the R1 position of Formula I are preferred; examples of such compounds are found in Table 2, namely GLN-1062, GLN-1081, GLN-1082, GLN-1083, GLN-1084, GLN-1085, GLN-1086, GLN-1088, GLN-1089, GLN-1090, GLN-1091, GLN-1092, GLN-1093, GLN-1094, GLN-1095, GLN-1096, GLN-1097, GLN-1098, GLN-1099, GLN-1100, GLN-1101, GLN-1102, GLN-1103, GLN-1104, GLN-1105, GLN-1113.

In a particularly preferred embodiment the chemical substance of the present invention is characterised in that the substance is GLN-1062, whereby GLN-1062 is represented by

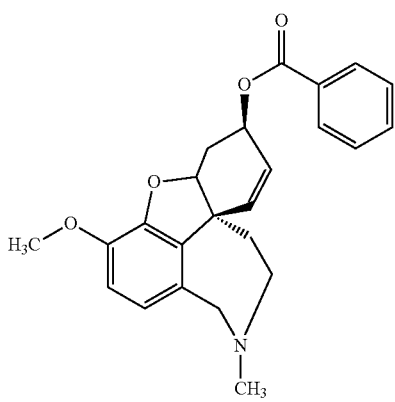

GLN-1062

The transmucosal administration of the present invention is based on the unexpected realisation that the compounds of the present invention exhibit relatively low stability when administered via oral administration. Cleavage of the ester group occurs in the gut and liver, in addition to other tissues of the body. The transmucosal administration provides an enhanced transport into brain and blood and corresponding enhanced efficacy by avoiding the first pass effect and cleavage of the prodrugs during passage through the gastro-intestinal tract and other organs.

Transmucosal administration of galantamine according to the prior art provides no such enhancement, as galantamine is not susceptible to cleavage by endogenous esterases. The surprising concept of the invention is based on the avoidance of cleavage of the prodrug post-administration but before partition via the BBB, thereby enhancing brain transport and increased relative concentration of the active substance after cleavage, which under conditions of the proposed routes of administration and drug formulations occurs primarily in the brain.

It was entirely surprising that the transmucosal administration of the prodrugs as described herein would lead to further enhancements in brain delivery of the prodrug and ultimately (after cleavage of the prodrug) to an effective dose of galantamine in the brain of subjects.

The invention therefore relates to a chemical substance for use as a medicament in the treatment of brain disease associated with cognitive impairment as described herein, wherein transmucosal administration provides avoidance and/or reduction of post-administration cleavage of the ester group of said substance by endogenous esterases.

This aspect of the invention represents a novel technical effect not previously disclosed or suggested in the art. The relatively low stability of the ester moiety of Memogain in the gastro-intestinal tract and liver has not been previously described in the art. A skilled person would therefore not have attempted to provide the modes of administration, or the salts as described herein, in order to improve delivery of the uncleaved compound to the brain. As demonstrated in the examples provide herein, the recognition of post-administration cleavage after oral administration in form of tablets has enabled the provision of the transmucosal administration of the invention, in addition to the salts as described herein.

The avoidance of in vivo esterase cleavage—with regard to the significant improvements obtained by transmucosal administration and the enhanced delivery of the salts described herein—enables treatment of patients who previously have avoided treatment with ChE inhibitors due to strong gastro-intestinal side effects associated with orally administered tablets. The improved brain delivery via transmucosal administration, in particular of high concentration aqueous solutions of Memogain salts, permits dosage regimes which were until now simply not possible with either galantamine itself (due to significant side effects) or Memogain (due to in vivo degradation).

Despite showing promising effects, galantamine treatment is associated with low compliance (of approximately 30%) due to strong unwanted side effects, indicating the strong need in the field for more sustainable therapeutic approaches. The administration routes and salts described herein enable treatment regimes with Memogain and its active principle galantamine that have never been achieved before, potentially enabling treatment of severe neurodegenerative disease—in patients who previously were not able to be effectively treated due to unwanted side effects—with the means and methods of the present invention.

In a preferred embodiment the chemical substance of the present invention is characterised in that the chemical substance is present as a salt, preferably a lactate, gluconate, maleate or saccharate salt.

In a preferred embodiment the salt comprises of stoichiometric and/or non-stoichiometric salts and/or hydrates of the chemical substances according to Formula I, II or III, whereby the salt is preferably described as:

Substance of Formula I, II or III.n HX.m H2O, whereby n, m=0-5 and n and m can be the same or different, and HX=an acid, selected preferably from lactic acid, gluconic acid, maleic acid or saccharic acid.

The invention also relates to a chemical substance for use as a medicament in the treatment of brain disease associated with cognitive impairment, wherein the chemical substance is the saccharate salt of GLN 1062. The saccharate salt of the present invention enables surprisingly high concentrations of up to 70% in water, providing an improved stable solution for high transmucosal doses of prodrug.

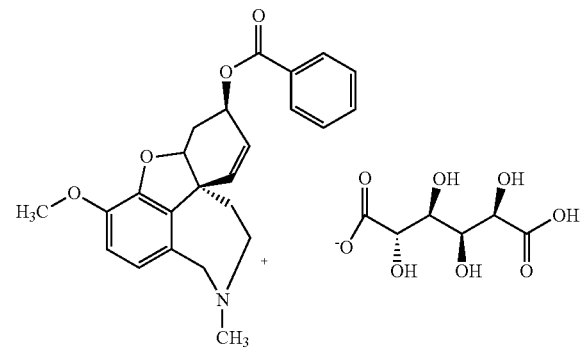

One preferred example of the invention relates to a chemical substance for use as a medicament in the treatment of brain disease associated with cognitive impairment, wherein the chemical substance is the gluconate salt of GLN-1062.

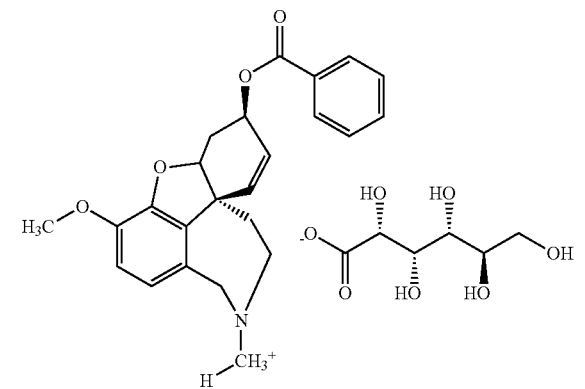

The gluconate salt of GLN 1062 has a high solubility, of 40% and more in water, especially in temperatures of around 25 to 50 degrees C. This high solubility at elevated temperatures can be used to produce high concentration liquid solutions of the gluconate salt of GLN 1062, which is relatively stable and can be administered for some days after creation of the solution.

The invention also relates to a chemical substance for use as a medicament in the treatment of brain disease associated with cognitive impairment, wherein the chemical substance is the maleate salt of GLN 1062.

The invention also relates to a chemical substance for use as a medicament in the treatment of brain disease associated with cognitive impairment, wherein the chemical substance is the lactate salt of GLN 1062.

The salts of the present invention also additionally show the surprising property of improved taste (reduced bitterness), reducing the need for taste masking components in the composition. The salts of the invention also show reduced numbing effects, such are as known for galantamine, when administered transmucosally. Due to their fast and efficient uptake the numbing (analgesic) effect and poor taste are reduced compared to those compositions described in the art.

In one embodiment the chemical substance of the present invention is characterised in that the chemical substance has solubility in water of at least 10%, preferably >20%, or more preferably >30% weight per volume (w/v).

The enhanced solubility of the salts as described herein represents a surprising and beneficial development. The solubility of the salts described herein enables higher concentrations of the compound to be administered in smaller volumes, thereby further enhancing the direct administration to the brain via transmucosal administration as described herein.

The transmucosal administration in combination with the salts of the prodrugs of the present invention exhibits a synergistic effect. The enhanced solubility allows higher concentrations of chemical substance to be administered, thereby enabling larger amounts of the active substance after cleavage (galantamine) to be active in the brain. The transport of substance (measured either by substance itself in the brain or by galantamine levels in the brain after cleavage of the prodrug) is greater than the expected sum of effects of transmucosal administration, administration of salts and administration of the prodrug when considered individually.

The prodrug properties of the compounds described herein are exploited and enhanced in a synergistic manner by the transmucosal application of their salts. The transmucosal administration of salts of prodrugs (with high solubility) provides a unique combination of administration parameters that enable dosage regimes previously not possible with galantamine, or salts of galantamine.

In one embodiment the present invention is characterised in that the chemical substance is administered at a dosage of from 0.1 to 200 mg, 1 to 100 mg, preferably 2 to 40 mg, preferably from one to three times daily, more preferably twice daily, and even more preferably only once daily.

The dosage regimes as described herein represent novel and surprisingly beneficial developments in comparison to the prior art with respect to effective galantamine treatment. The biological and medical effect of galantamine has never previously been tested with regard to the potential effect generated by administration at high doses. Many patients in need of galantamine treatment have not been able to be treated due to the significant side effects that occur with regular doses of galantamine. In order to obtain meaningful levels of galantamine in the brain of subjects, the prior art teaches high but also highly toxic doses. Because only a small fraction of orally or intranasally administered galantamine drug reaches the brain, the dose required to show an effect during treatment of brain disease is often intolerably high due to the large amount of galantamine in other tissues of the body, thereby causing unwanted side effects.

The dosages of the present invention are enabled by the transmucosal administration of the prodrugs disclosed herein. Due to enhanced brain delivery of the hydrophobic prodrugs, in combination with further enhanced delivery due to transmucosal administration, smaller doses of the prodrug are required in order to achieve the same or greater effect of galantamine in the brain after prodrug cleavage and release of the active compound. It is entirely surprising that also lower doses of the prodrugs of the invention, for example GLN 1062, within the ranges of the invention, lead to more pronounced and/or more potent effect in cognitive recovery compared to oral administration of galantamine.

These dosage regimes are particularly beneficial when administered in the form of salts of the compounds as described herein.

In one embodiment the invention relates to a chemical substance as described herein for use as a medicament in the treatment of brain disease associated with cognitive impairment, wherein the chemical substance or salt thereof is administered intranasally, bucally or sublingually as a 2 to 40% weight per volume (w/v) solution at an amount of 20 to 100 microliters, preferably in a single (intranasal or oral) spray event, one to three times daily.

At these doses effective cognitive recovery is possible in patients with brain diseases with no (or only very minor) observable side effects. It was at the time of the invention unexpected, that through the combination of prodrug (preferably GLN 1062) and transmucosal administration such dosages could lead to an effective galantamine treatment through a dosage regime comprising a relatively small number of administration events of relatively small volumes of active compound (via sprays or administration of oral transmucosal formulations).

In one preferred embodiment the invention relates to a chemical substance as described herein for use as a medicament in the treatment of brain disease associated with cognitive impairment, wherein the chemical substance or salt thereof is administered intranasally, bucally or sublingually as a 10% weight per volume (w/v) solution at an amount of 50 microliters, preferably in a single (intranasal or oral) spray event, one to three times daily.

In one embodiment the invention relates to a chemical substance as described herein for use as a medicament in the treatment of brain disease associated with cognitive impairment, wherein the brain disease to be treated is Alzheimer's and/or Parkinson's disease, the chemical substance is the gluconate or saccharate salt of GLN 1062, which is administered intranasally, bucally or sublingually as a 2 to 40% weight per volume (w/v) solution at an amount of 20 to 100 microliters, preferably in a single (intranasal or oral) spray event, one to three times daily.

The salt formulations of GLN 1062 show surprisingly high solubility, allowing high doses of GLN 1062 to be applied with ease by the patients themselves in small volumes, providing therapeutically relevant results without the need for much higher doses of the prodrugs or their active parent drug galantamine and without the occurrence of significant side effects.

In one embodiment the invention relates to a chemical substance as described herein for use as a medicament in the treatment of brain disease associated with cognitive impairment, wherein the brain disease to be treated is Alzheimer's disease, the chemical substance is the gluconate salt of GLN 1062, which is administered intranasally, bucally or sublingually as a 10% weight per volume (w/v) solution at an amount of 50 microliters, preferably in a single intranasal spray event, twice daily.

In one embodiment the chemical substance of the present invention is characterised in that intranasal application is carried out by administering a therapeutically effective amount of the chemical substance using a suitable metered dose device such as a atomizer, sprayer, pump spray, dropper, squeeze tube, squeeze bottle, pipette, ampule, nasal cannula, metered dose device, nasal spray inhaler, nasal continuous positive air pressure device, and/or breath actuated bi-directional delivery device.

In one embodiment the invention relates to a chemical substance as described herein for use as a medicament in the treatment of brain disease associated with cognitive impairment, wherein the sublingual administration is carried out by administering a therapeutically effective amount of the chemical substance under the tongue by placing one or more drops of a solution, or an amount of particulate in the form of freeze-dried powder or emulsion underneath the tongue and/or by spraying the underside of the tongue with a preselected volume of a liquid composition comprising the chemical substance.

In one embodiment the invention relates to a chemical substance as described herein for use as a medicament in the treatment of brain disease associated with cognitive impairment, wherein the buccal administration is carried out by administering a therapeutically effective amount of the chemical substance to the buccal vestibule inside the mouth between the cheek and the gums as a freeze-dried powder or emulsion, or an orally disintegrating or orodispersible tablet (ODT).

In one embodiment the chemical substance of the present invention is characterised in that the subject is a mammal, preferably a human.

In one embodiment the chemical substance of the present invention is characterised in that the brain disease to be treated is selected from Alzheimer's and/or Parkinson's disease, other types of dementia, schizophrenia, epilepsy, stroke, poliomyelitis, neuritis, myopathy, oxygen and nutrient deficiencies in the brain after hypoxia, anoxia, asphyxia, cardiac arrest, chronic fatigue syndrome, various types of poisoning, anaesthesia, particularly neuroleptic anaesthesia, spinal cord disorders, inflammation, particularly central inflammatory disorders, postoperative delirium and/or subsyndronal postoperative delirium, neuropathic pain, abuse of alcohol and drugs, addictive alcohol and nicotine craving, and/or effects of radiotherapy.

In one embodiment the chemical substance of the present invention is characterised in that the distribution of the chemical substance in a patient after administration exhibits a brain-to-blood concentration ratio of more than 5, preferably more than 10, more preferably between 15 and 25.

The invention further relates to the use of the chemical substance as described herein for the treatment of brain disease associated with cognitive impairment by administering a therapeutically effective amount of said chemical substance by a transmucosal route selected from the group consisting of intranasal, buccal and/or sublingual administration.

In another aspect the present invention relates to a pharmaceutical composition comprising the chemical substance according to Formula I, II or GLN 1062 of the present invention and preferably one or more pharmaceutically acceptable carriers for use in the treatment of brain diseases associated with cognitive impairment in a mammal, characterised in that the composition is suitable for intranasal, buccal and/or sublingual application. The invention therefore relates to nose drops or under-the-tongue drops in the form of a liquid composition for transmucosal administration via nasal or buccal mucous membranes.

The invention relates to a pharmaceutical composition comprising the chemical substance according to Formula I, II or GLN 1062 of the present invention for use as a medicament in the treatment of brain diseases associated with cognitive impairment via transmucosal administration, wherein the composition is an aqueous solution, comprising 2 to 40%, preferably 5 to 15% and more preferably 10% weight per volume (w/v) of the chemical substance.

In one embodiment the invention relates to a pharmaceutical composition, wherein the composition comprises N-ethylpyrrolidone. In a preferred embodiment the invention relates to a pharmaceutical composition, wherein the composition comprises a self-microemulsifying drug delivery (SMEDD) system. Such compositions preferably comprise glyceryl caprylate, polyethyleneglycol, propyleneglycol and/or diethyleneglycolemonoethylether.

The invention also relates to a pharmaceutical composition comprising the chemical substance according to Formula I, II or GLN 1062 of the present invention for use as a medicament in the treatment of brain diseases associated with cognitive impairment via transmucosal administration, wherein the composition comprises a sustained release formulation comprising chitosan.

A further embodiment of the invention relates to a pharmaceutical composition comprising a micronized powder formulation of the chemical substance to be administered, preferably with a particle size of 0.01 to 1000 microns, preferably 0.1 to 100 or 1 to 10 microns.

The invention relates to a pharmaceutical composition comprising the chemical substance according to Formula I, II or GLN 1062 of the present invention for use as a medicament in the treatment of brain diseases associated with cognitive impairment via transmucosal administration, wherein the composition comprises a sublingual tablet, preferably comprising lactose monohydrate, corn starch, polyvinylpyrrolidone (PVP) and/or magnesium stearate, and optionally with a flavouring agent. Alternatively the composition may comprise a sublingual tablet comprising mannitol, sodium starch glycolate, croscarmellose, ascorbic acid and/or magnesium stearate, optionally with a flavouring agent.

The invention also relates to a pharmaceutical composition comprising the chemical substance according to Formula I, II or GLN 1062 of the present invention for use as a medicament in the treatment of brain diseases associated with cognitive impairment via transmucosal administration, wherein the composition comprises a multi-layered tablet with digestive acid resistant coating, such as comprising eudragit.

In a preferred embodiment the pharmaceutical composition of the invention comprises the substance to be administered at 2 to 40% weight per weight (w/w), preferably 10 to 30%, or more preferably 5, 10, 20 or 30% weight per weight (w/w) in a composition in the form of a self-microemulsifying drug delivery (SMEDD) system, sustained release formulation comprising chitosan, micronized powder formulation or sublingual or buccal tablet.

In a particularly preferred embodiment, the CNS therapeutic is the established anti-dementive drug galantamine, the pro-drug is the benzoic ester of galantamine (galantamine benzoate, GLN 1062, otherwise mentioned as "Memogain"), and the salt forms used for intranasal delivery are preferably the lactate, gluconate, maleate or saccharate salts of said benzoylester of GLN 1062. GLN 1062 is also known as (4aS,6R,8aS)-4a,5,9,10,11,12-hexahydro-3-methoxy-11-methyl-6H-Benzofuro[3a,3,2-ef][2]benzazepin-6-ol, 6-benzoate. For example, the gluconate salt of Memogain is also known as the galantamine benzoate gluconate.

The invention also relates therefore to a method of treatment for brain disease associated with cognitive impairment by administering a therapeutically effective amount of the above described chemical substances by a transmucosal route selected from the group consisting of intranasal, buccal and/or sublingual administration. The method of treatment of the present invention may also be further defined by embodiments of the invention provided herein with respect to the administration regime, the substance itself and/or other administration parameters.

DETAILED DESCRIPTION OF THE INVENTION

A detailed description of the present invention encompasses the following developments:

(1) In preferred embodiments pro-drugs of galantamine are provided that are significantly more lipophilic than their parent compounds, thereby enhancing their passive transport through the blood-brain barrier (BBB) into the brain.

(2) These pro-drugs are pharmacologically inactive and hence do not produce any significant GI or other side effects, as long as they remain un-cleaved in the particular tissue. After enzymatic cleavage, from each molecule of pro-drug one molecule of parent drug is formed, thereby producing the full pharmacological effect of the drug. If cleavage is preferentially in the brain, due to enhanced distribution into this organ, and the availability of suitable endogenous enzyme(s) therein, a significantly higher concentration of drug at the target sites in the CNS and consequently larger medically beneficial effects are achieved.

(3) Preferential transport to the target organ brain is further optimized in a surprising and beneficial manner by transmucosal routes of administration in the oral or nasal cavity.

(4) High-dose formulations and extended-release formulations of the pro-drugs further optimize the pharmacokinetics of uptake into the brain and maintain drug levels therein for optimal effectiveness of action.

Taken together, these features of the formulations of pro-drugs described herein, foster delivery to the brain of much higher concentrations of drug than can be achieved by oral administration in form of tablets of the unmodified drug. The improved distribution of the drug to the brain dramatically reduces all locally produced side effects in the GI tract, thereby permitting to immediately apply an efficacious dose of the drug to its CNS-located target molecules, e.g. nicotinic receptors and cholinesterases.

As the blood-brain barrier (BBB), located at the level of the brain capillaries, is the major barrier to the passage of drugs from the blood compartment to the brain, initial focus on optimizing penetration of the pro-drugs through the BBB yielded promising results. The brain microvessel endothelial cells forming the BBB have as typical morphological characteristics tight junctions between cells, absence of fenestrations and diminished pinocytotic activity. A variety of enzymes further contributes to the restrictive nature of the BBB. The ability of drugs to cross the BBB mostly depends on their physicochemical properties, such as their lipophilicity. Consequently, the compounds considered in the present disclosure all are pro-drugs with improved lipophilicity, in comparison to their parent compounds.

The BBCR is to be understood as the brain-to-blood concentration ratio after transport equilibrium via the BBB has been achieved.

In general, a Log P value of a galanthamine derivative of approximately 1.3 leads to a BBRC (brain-to-blood concentration ratio) of approximately 2 or somewhat less than 2, a log P value of approx. 2 leads to a BBRC of approx. 5 to 10 and a log P value of approx. 3 leads to a BBRC of approx. 20 or over 20. This is intended as a guideline for comparing log P values with BBB permeability and may vary for some particular compounds. This guideline does not represent a limiting feature of the invention.

Pro-drugs are defined as per se therapeutically inactive agents that are predictably transformed in specific locations in the body to active metabolites. In this sense, pro-drugs are inactive precursors of parent drugs that undergo transformation into active agents in vivo by enzymatic cleavage or chemical spontaneous process(es) in a predictable fashion. In the pro-drugs discussed here, there exists preferably a covalent ester linkage between the parent drug and the selected transport pro-moiety, and upon cleavage of this ester bond, ideally in the target organ brain, the inactive pro-drug releases the active parent drug at or close to its target sites in the CNS.

Rapid absorption in the oral cavity is best achieved by sublingual administration, as the mucosal thickness in this area is lower than in other buccal areas, in addition to being significantly less keratinized (Shojaei A (1998) Buccal mucosa as a route for systemic drug delivery: a review. J Pharm Pharmaceut Sci 1: 15-30). Fast dissolving sublingual formulations, such as rapidly degrading tablets or liquid-filled capsules, can additionally help reducing enzymatic degradation of pro-drug in saliva. The nasal cavity also provides a promising starting point for alternative administration regimes, with its large surface area, high vasculature and low enzymatic environment. Intranasal delivery is capable of providing a similarly high level of bioavailability as intravenous administration with the advantages of non-invasiveness, ease of self-administration, patient comfort and patient compliance in comparison to the latter. These advantages may have been known generally by practitioners of the art; however, significant hurdles remain for developing such application routes. For chronic systemic delivery, the problems of epithelial damage and toxicity need to be solved, and that for sufficient bioavailability high concentrations of drug in small volumes of vehicle are provided. This requires first selection of suitable chemical compounds that enable the required formulations and concentrations, in addition to finding appropriate methods for administration and finally developing preferred salts and/or solutions thereof that allow optimal administration of effective substance to the brain.

It was therefore not predictable in light of the prior art, which compounds would provide successful outcomes with regard to alternative administration modes. It can also not be predicted from the prior art, which salts and/or formulations could be generated for the prodrugs of this invention, nor whether these products would provide an effective BBB penetration and cleavage to active substance in the brain.

Suitable pro-drug formulations according to the invention were selected as follows. By way of monitoring the concentrations of the pro-drug in whole brain and blood plasma after intravenous injection of the pro-drug into animals, we determined their basic BBCR.

By additionally monitoring the concentrations of the released parent drug in brain and blood, we determined the rates and effectiveness of conversion from pro-drug to drug. These studies demonstrated that uptake of pro-drug into the brain was very fast indeed, and that the fast uptake strongly favored conversion of pro-drug to drug to take place in the brain. As most of the parent drugs under study are known to act as cholinesterase inhibitors, we reasoned and then proved that the related pro-drugs are cleaved to their active parent drugs by esterases of the butyrylesterase and carboxyesterase type.

We then changed to transmucosal delivery in the oral and nasal cavity and determined in animal models again the kinetics of uptake into the brain, the drug levels achieved therein, and the pharmacodynamics achieved in comparison to oral delivery of the derivative and parent drug. The administration of the chemical substances described herein via transmucosal routes represents a surprising and unexpected advantage in comparison to previously known methods of oral administration. It was neither disclosed nor suggested in the prior art that certain derivatives of galantamine could be preferentially transported into the brain via transmucosal administration. As described above, previous attempts of intranasal application of galantamine had failed due to poor physicochemical properties. Surprisingly, the transmucosal application of the galantamine derivatives as described herein as preferred chemical substances does enable improved brain-to-blood concentration ratios. This effect is surprising in light of the previous failures of similar administration regimes for galantamine itself.

A goal of the present invention is therefore to present novel CNS therapeutics having optimal brain bioavailability due to being formulated as lipophilic pro-drugs and administered via transmucosal absorption pathways in the oral or nasal cavity The invention is based on the fundamental understanding that the base compound itself, i.e. galantamine, has to be delivered to the brain by crossing the blood-brain barrier. Due to the fact that galantamine itself has a very low Log P value and therefore is not able to pass the blood brain barrier in sufficiently effective amounts, it is necessary to modify the base compound in a manner which makes the substance more lipophilic in order to more efficiently cross the blood-brain barrier. Once the substance has reached the brain, the modified base compound, preferably a chemical substance (CS) according to formula I or II, is reconverted by enzymatic cleavage of the ester bond on the R1 residue to the effective base compound itself, namely galantamine.

An aim of the invention is to deliver the chemical compound in a way into the brain to make sure that an effective amount of the base compound (after cleavage within the brain following crossing the blood-brain barrier) is available in the brain, in particular in order to ensure higher bioavailability of the later base compound galantamine.

As previously described (Maelicke et al., Memogain is a galantamine Pro-drug having Dramatically Reduced Adverse Effects and Enhanced Efficacy, J Mol Neurosci (2010) 40:135-137) the substance according to formula I is an inactive pro-drug of galantamine having more than 10-fold higher bioavailability in the brain than the same doses of galantamine. Said derivative of galantamine can be obtained by a one-step chemical modification of the parent drug (galantamine). The modification almost completely abolishes the pharmacological activity of galantamine on its two major targets in the human body, nicotinic acetylcholine receptor (nAChR) and acetylcholinesterase (AChE).

At the physiologically interesting concentration of 1 µM, Memogain has less than 4% of the esterase inhibition induced by the same concentration of galantamine.

Synthesis, preparation and pharmacokinetic data of the substance according to formula I are previously described in detail in WO 2009/127218 A1 as well as in US 2009/0253654 A1, both are herewith incorporated by reference.

It is preferred to administer the chemical substance of the present invention by a route selected from the group consisting of intranasal, buccal, including sublingual, and/or intravenous administration. This way of administration guarantees a relative short bio-transport from the site of application, namely mouth, nose, tongue, buccal, intravenous, to the brain. Therefore the chance of disintegration of the chemical substance is low and the likelihood of effective transport from the nearby place of application to the blood-brain barrier is high.

In a preferred embodiment, the chemical substance is used as a salt, preferably a quaternary ammonium salt, preferably a lactate, gluconate, maleate or saccharate salt, having a solubility in water of at least 10%, preferentially of more than 20%.

It is intended to use the chemical substance in manner that enables distribution of the chemical substance in a patient after administration at a brain-to-blood concentration ratio of more than 5, preferably more than 10, more preferably between 15 and 25.

In a preferred embodiment, the CNS therapeutics are galantamine and structurally related compounds, the prodrugs are aliphatic, aromatic and heteroaromatic esters of alcoholic OH-groups being essential for the pharmacological activity of the therapeutics. To be suitable for transmucosal delivery in the oral or nasal cavity, they are formulated as high-concentration aqueous salt solutions, or as emulsions, or as selfmicroemulsifying drug delivery systems (SMEDDs) or as micronized powder formulations. It was surprising, that the pharmaceutically applicable solutions of Memogain salts fulfilled the criteria for appropriate stability, concentration, pH, osmolarity, small and nasal mucosal tolerance in solution for intranasal application, as described in the following table 1.

membrane. The transmucosal routes of administration of the present invention are defined as intranasal, buccal and/or sublingual.

Nasal or intranasal administration relates to any form of application of the prodrug or pharmaceutical composition thereof to the nasal cavity. The nasal cavity is covered by a thin mucosa which is well vascularised. Therefore, a drug molecule can be transferred quickly across the single epithelial cell layer without first-pass hepatic and intestinal metabolism. Intranasal administration is therefore used as an alternative to oral administration of for example tablets and capsules, which lead to extensive degradation in the gut and/or liver.

Buccal administration relates to any form of application that leads to absorption across the buccal mucosa, preferably pertaining to adsorption at the inside of the cheek, the surface of a tooth, or the gum beside the cheek.

Sublingual administration refers to administration under the tongue, whereby the chemical comes in contact with the mucous membrane beneath the tongue and diffuses through it.

Pharmaceutical compositions suitable for buccal and/or sub-lingual administration may comprise additional pharmaceutically acceptable carriers, for example a buccal dosage unit may comprise the active agent to be administered in addition to a polymeric carrier that bioerodes and provides for delivery of the active agent over a predetermined time period, and, preferably, a lubricant, such as magnesium stearate. Additional carrier agents are known to one in the art. This active agent can be physically compounded with materials of some or all of classes of ingredients that function as pH controls, preservative agents, viscosity control agents, absorption enhancers, stabilizing agents, solvents, and carrier vehicles. Such agents may be present in either solid or liquid forms of the pharmaceutical composition.

A self-microemulsifying drug delivery system (SMEDDS) may be present in said pharmaceutical compo-

TABLE 1

| Acceptance criteria | Preclinic | Phase 1 | Market |
|---|---|---|---|
| Desired maximal concentration | 25% | 25% | 10% |
| Acceptable maximal concentration | 20% | 10% | 5% |
| pH | 4.5-7 | 5-6.5 | 5-6.5 |
| Chemical stability | >3 hours | >7 days | >2 years |
| Stability of solution | >3 hours | >7 days | >2 years |
| % F in rat | >80% | n.a. | n.a. |
| Osmolarity | >250 mosmol/l | >250 mosmol/l | >250 mosmol/l |
| Smell | not unpleasant | not unpleasant | not unpleasant |
| Tolerance of nasal mucosa | no significant irritation during 28-day repeat dose study in rat & dog | no irritation in human | no irritation in human over period of administration |

The pharmaceutical composition is preferably an aqueous solution, comprising 2 to 20% weight per volume (w/v), preferably 5 to 15% weight per volume (w/v), more preferably 10% weight per volume (w/v) of the chemical substance. To be suitable for transmucosal delivery in the oral or nasal cavity, they are formulated as high-concentration aqueous salt solutions, or as emulsions, or as selfmicroemulsifying drug delivery systems (SMEDDs) or as micronized powder formulations.

The term transmucosal administration relates to the entering of a pharmaceutical agent through, or across, a mucous sition, meaning a drug delivery system that uses a microemulsion achieved by chemical rather than mechanical means. That is, by an intrinsic property of the drug formulation, rather than by special mixing and handling. It employs the familiar effect displayed by anethole in many anise-flavored liquors. Microemulsions have significant potential for use in drug delivery, and SMEDDS (including so-called "U-type" microemulsions) are the best of these systems identified to date. SMEDDS are of particular value in increasing the absorption of lipophilic drugs taken by mouth. SMEDDS in may include in a non-limiting manner include formulations of the drugs anethole trithione, oridonin, curcumin, vinpocetine, tacrolimus, berberine hydrochloride, nobiletin and/or piroxicam.

The salt relates to any salt of the compounds of formulae I-II or of GLN 1062 itself. The term salt preferably refers to compounds comprising a protonated, positively charged N atom in the 7-member ring structure of the base compound.

"Administration" or "treatment," as it applies to an animal, human, experimental subject, cell, tissue, organ, or biological fluid, refers to contact of a pharmaceutical, therapeutic, diagnostic agent, compound, or composition to the animal, human, subject, cell, tissue, organ, or biological fluid. "Administration" and "treatment" can refer, e.g., to therapeutic, placebo, pharmacokinetic, diagnostic, research, and experimental methods. "Treatment," as it applies to a human, veterinary, or research subject, refers to therapeutic treatment, prophylactic or preventative measures, to research and diagnostic applications.

The invention encompasses administration of an effective amount of chemical substance as described herein to a patient in need thereof. "Effective amount" or "therapeutically effective amount" means an amount sufficient to ameliorate a symptom or sign of a disorder or physiological condition or an amount sufficient to permit or facilitate a diagnosis of the disorder or physiological condition. An effective amount for a particular patient or veterinary subject may vary depending on factors such as the condition being treated, the overall health of the patient, the method route and dose of administration and the severity of side effects. An effective amount can be the maximal dose or dosing protocol that avoids significant side effects or toxic effects. The effect will result in an improvement of a diagnostic measure, parameter, or detectable signal by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject. "Effective amount" also relates to an amount of the prodrug substance or pharmaceutical composition thereof, sufficient to allow or facilitate the amelioration and/or diagnosis of a symptom or sign of a disorder, condition, or pathological state.

Preferred chemical substances according to the present invention are provided in Table 2.

TABLE 2

| molregno | molstructure | abbrev. |
|---|---|---|
| GLN-1062 | 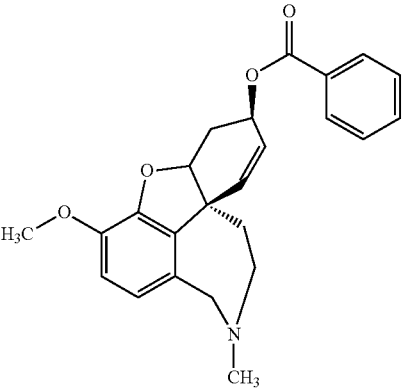 | Bz-Gal |
| GLN-1081 | 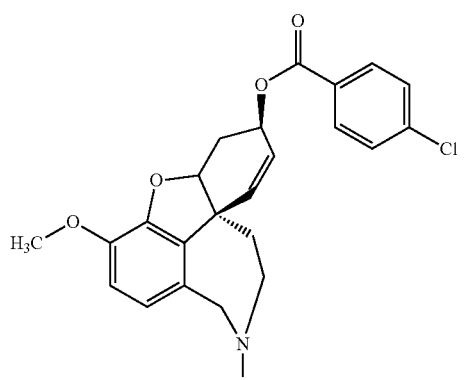 | 4-Cl-Bz-Gal |

TABLE 2-continued
| molregno | molstructure | abbrev. |
|---|---|---|
| GLN-1082 | 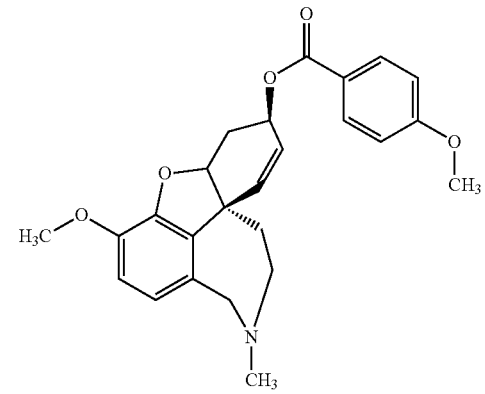 | 4-MeO-Bz-Gal |
| GLN-1083 | 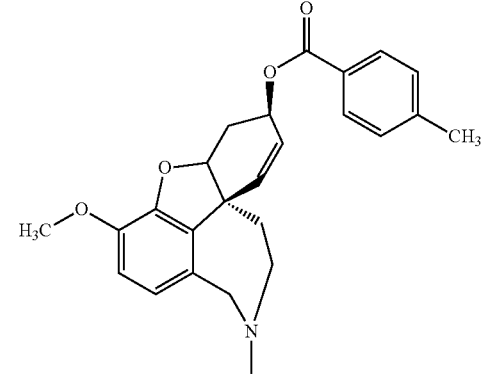 | 4-Me-Bz-Gal |
| GLN-1084 | 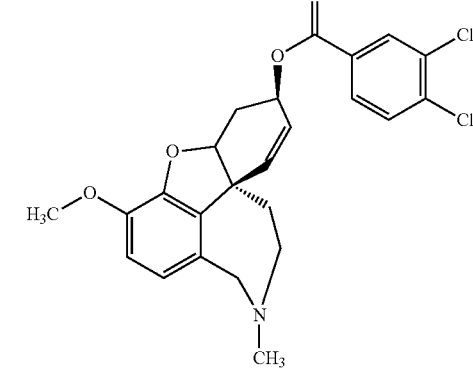 | 3,4-Cl2-Bz-Gal |
| GLN-1085 | 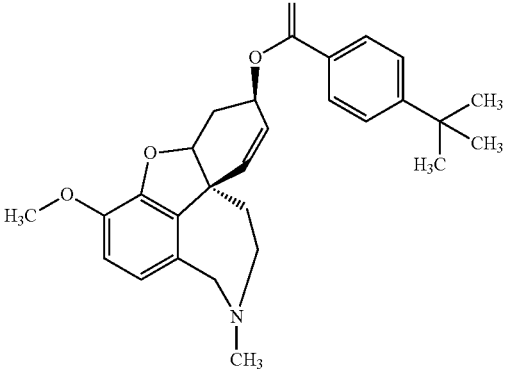 | 4-tBu-Bz-Gal |

TABLE 2-continued

| molregno | molstructure | abbrev. |
|---|---|---|
| GLN-1086 | | 3-CF3-4-Cl-Bz-Gal |
| GLN-1088 | | 4-CF3-Bz-Gal |
| GLN-1089 | | 2,4-Cl2-Bz-Gal |
| GLN-1090 | | 4-NO2-Bz-Gal |

TABLE 2-continued

| molregno | molstructure | abbrev. |
|---|---|---|
| GLN-1091 | | 3-Cl-Bz-Gal |
| GLN-1092 | | 3-CF3-Bz-Gal |
| GLN-1093 | | 3-NO2-Bz-Gal |
| GLN-1094 | | 3,5-Cl2-Bz-Gal |

TABLE 2-continued
| molregno | molstructure | abbrev. |
|---|---|---|
| GLN-1095 | 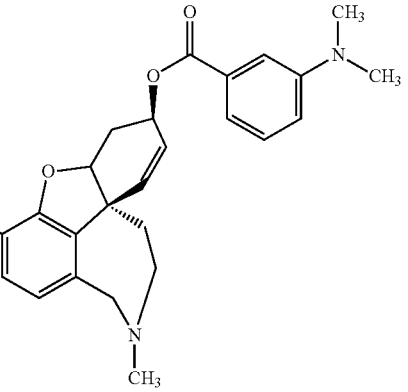 | 3-Me2N-Bz-Gal |
| GLN-1096 | 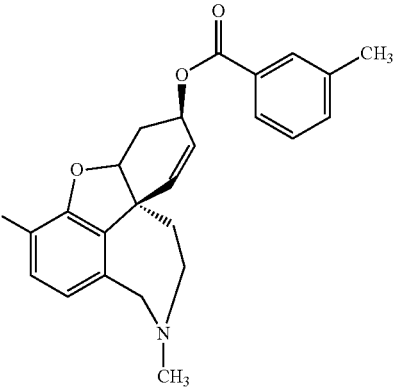 | 3-Me-Bz-Gal |
| GLN-1097 | 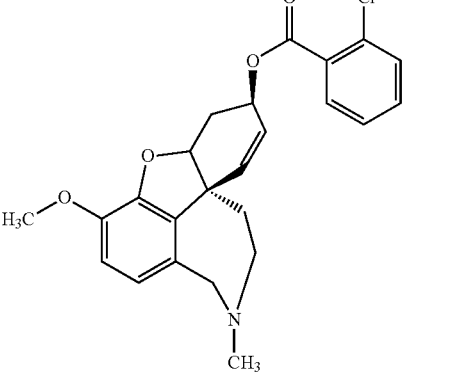 | 2-Cl-Bz-Gal |
| GLN-1098 | 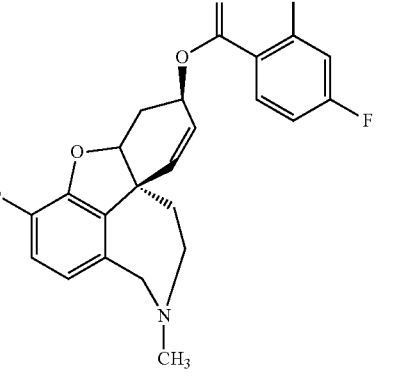 | 2,4-F2-Bz-Gal |

TABLE 2-continued

| molregno | molstructure | abbrev. |
|---|---|---|
| GLN-1099 | | 2,5-Cl2-Bz-Gal |
| GLN-1100 | | 4-F-Bz-Gal |
| GLN-1101 | | 4-NMe2-Bz-Gal |
| GLN-1102 | | 4-NH2-Bz-Gal |

TABLE 2-continued

| molregno | molstructure | abbrev. |
|---|---|---|
| GLN-1103 | | 3-Me-4-NMe2-Bz-Gal |
| GLN-1104 | | 3,4-OCH2O-Bz-Gal |
| GLN-1105 | | 4-Ac-Bz-Gal |

TABLE 2-continued

| molregno | molstructure | abbrev. |
|---|---|---|
| GLN-1113 | | 2-AcO-Bz-Gal |
| GLN-0993 | | n-Hex-Gal |
| GLN-1060 | | |

TABLE 2-continued

| molregno | molstructure | abbrev. |
|---|---|---|
| GLN-1061 | | |
| GLN-1106 | | 3-Th-Bz-Gal |
| GLN-1107 | | 2-Th-Bz-Gal |
| GLN-1108 | | 5-Cl-2-Th-Bz-Gal |

TABLE 2-continued

| molregno | molstructure | abbrev. |
|---|---|---|
| GLN-1109 | | 5-Im-Bz-Gal |
| GLN-1110 | | 5-OA-Bz-Gal |
| GLN-1111 | | 5-Th-Bz-Gal |
| GLN-0926 | | Nic-Gal |

FIGURES

The invention is further described by the figures. These are not intended to limit the scope of the invention.

FIG. 1: Powder diffraction diagram of Memogain gluconate obtained using dioxane.

Figure 2:
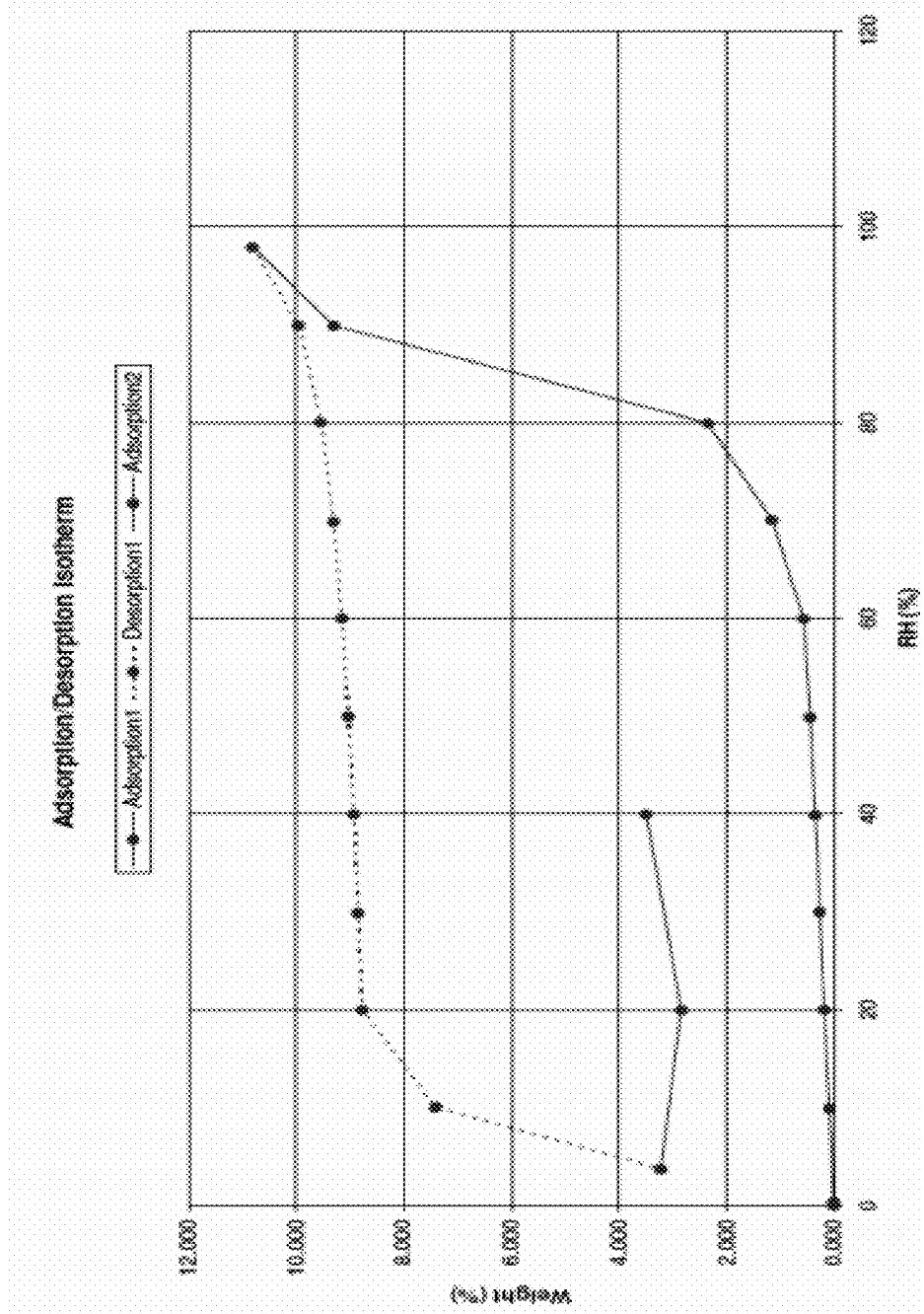

FIG. 2: Adsorption/desorption isotherm of Memogain gluconate monohydrate.

Figure 3:
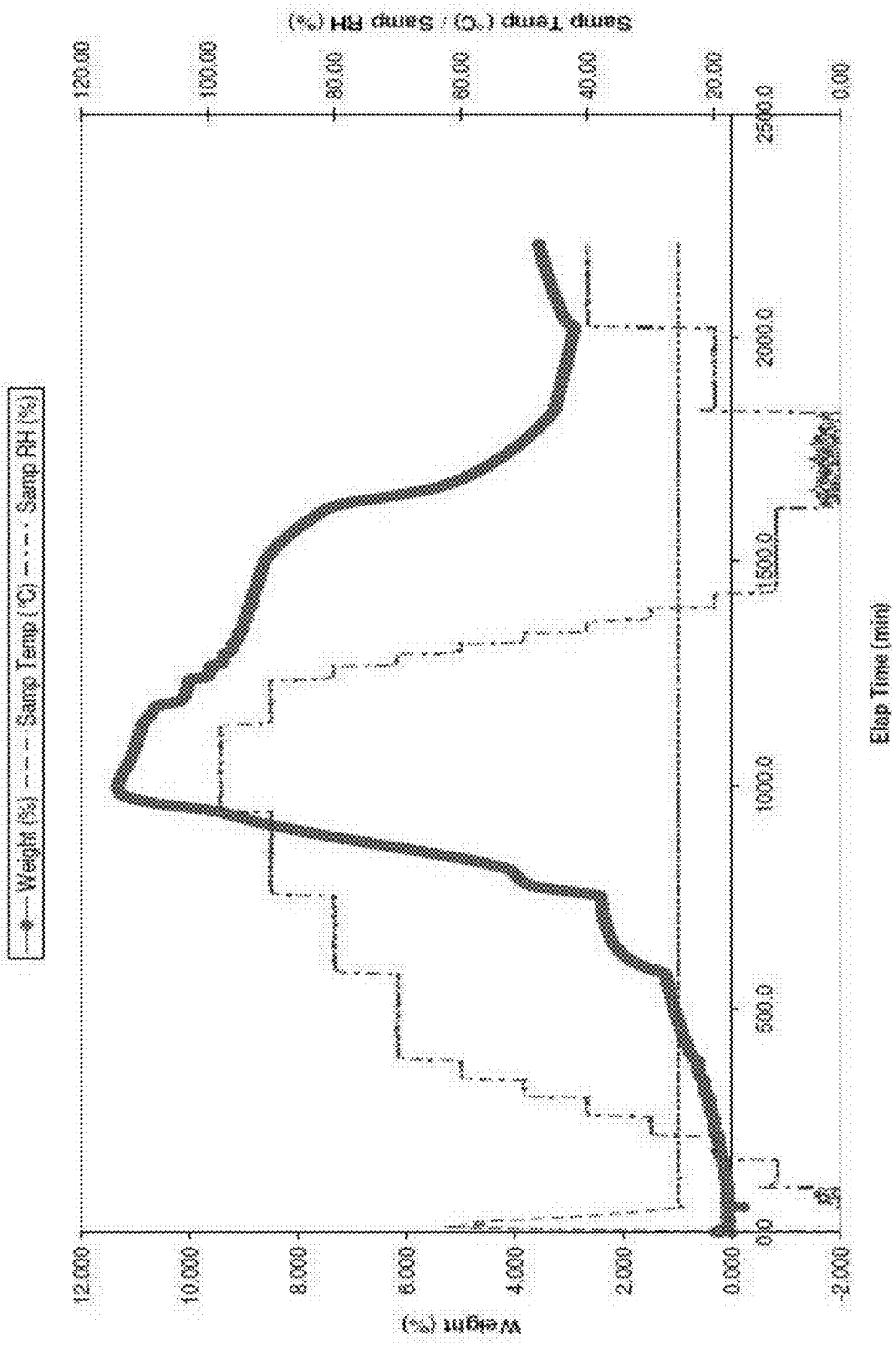

FIG. 3: Weight loss on heating of Memogain gluconate monohydrate.

Figure 4:
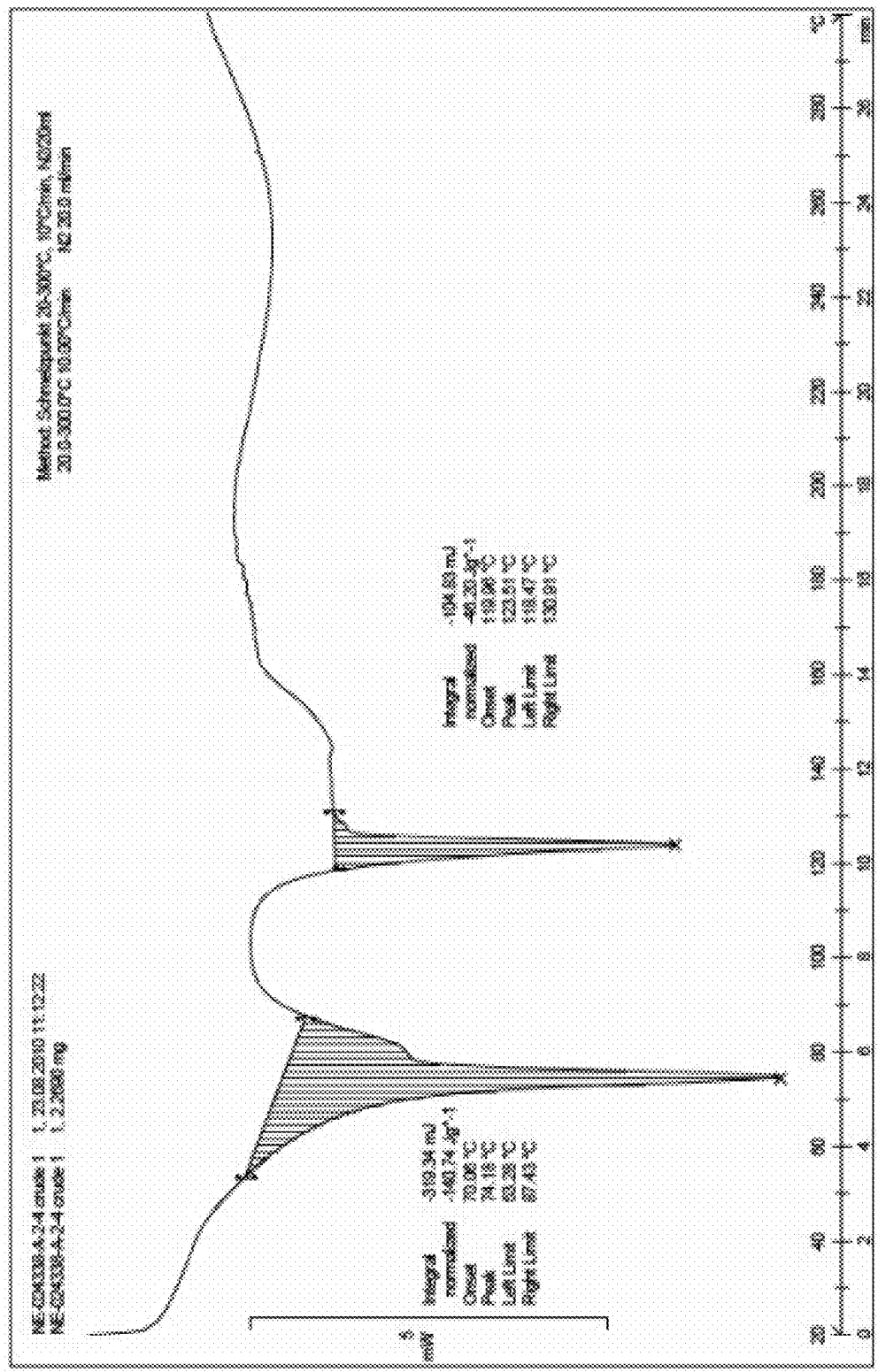

FIG. 4: Differential scanning calorimetry (DSC) the wet cake of Memogain gluconate.

Figure 5:
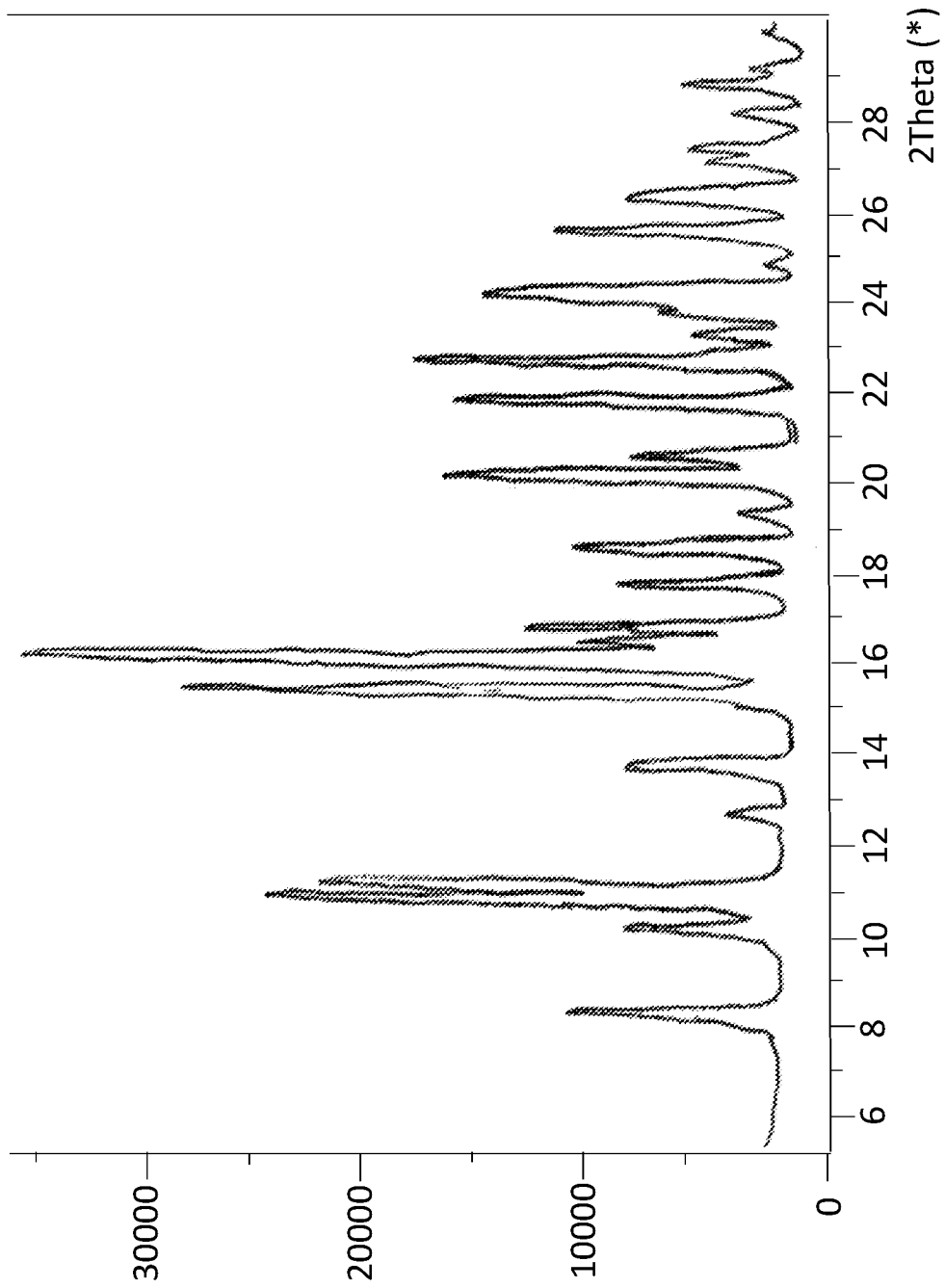

FIG. 5: Powder diffraction diagram of Memogain gluconate obtained using ethanol.

Figure 6:
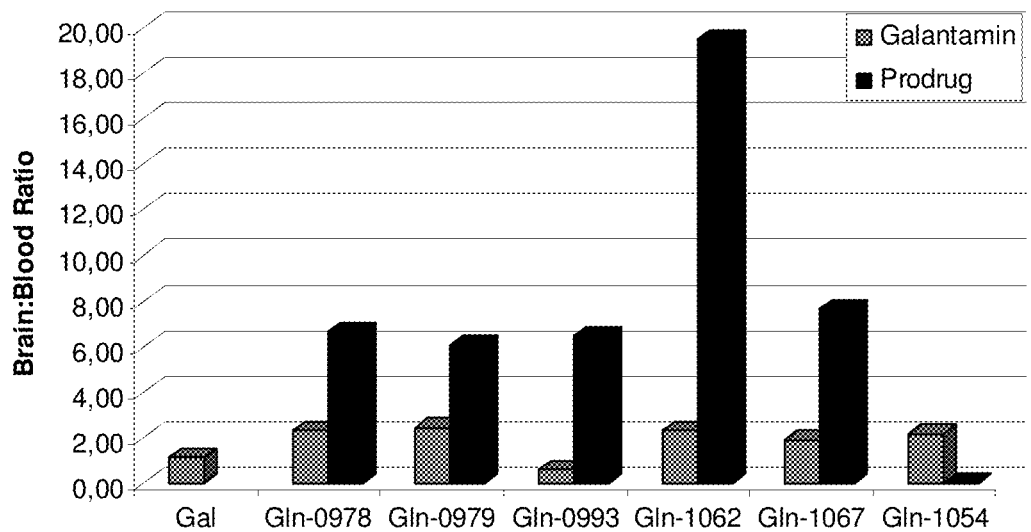

FIG. 6: Experimental brain-to-blood concentration ratios for galantamine and several pro-galantamines.

Figure 7:
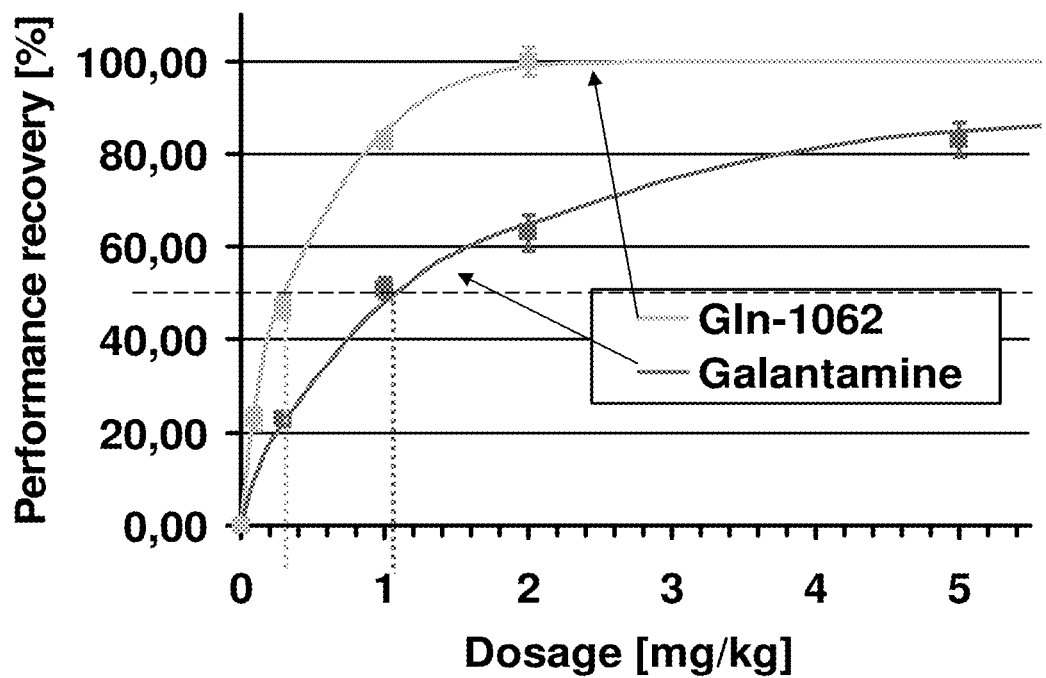

FIG. 7: Intranasal Memogain is more potent than galantamine. Mice were challenged with scopolamine and dosed with increasing concentrations of oral galantamine and intranasal Memogain before performance evaluation in the mouse T-maze model.

Figure 8:
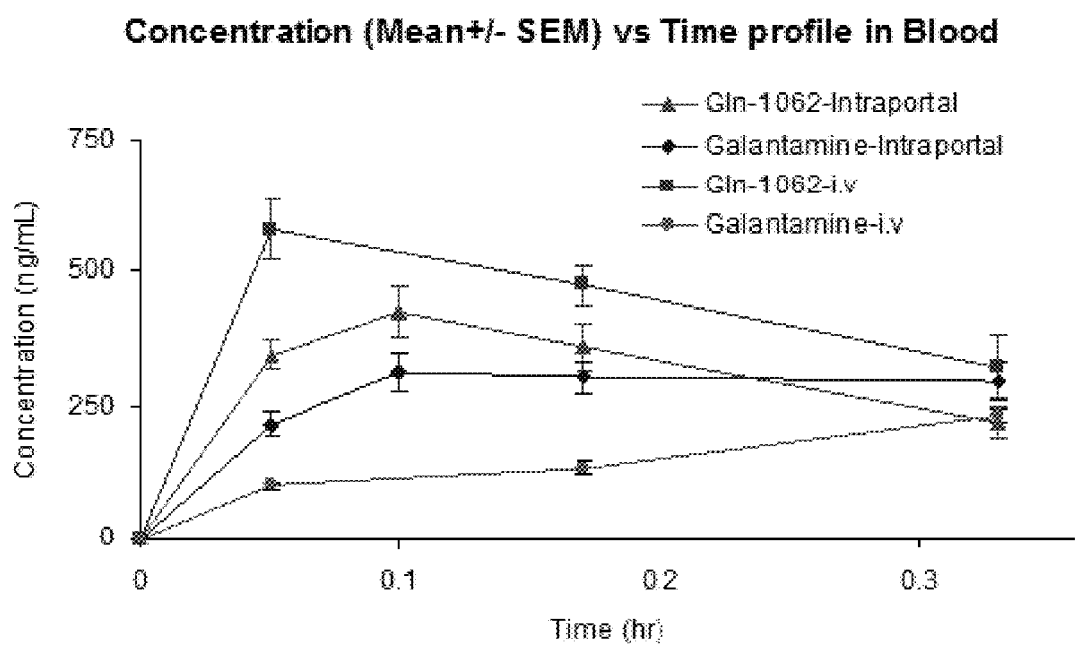

FIG. 8: The first-pass effect of Gln-1062 was evaluated after intravenous and intraportal dosing of 3 mg/kg in Wistar rats.

Figure 9:
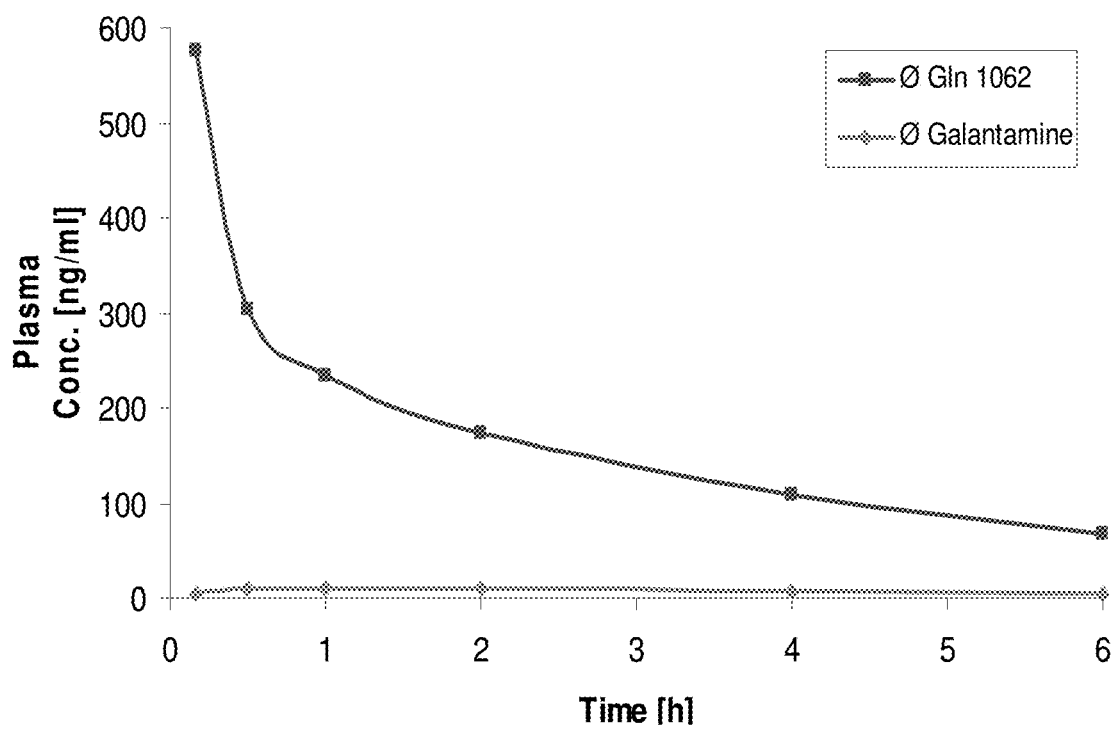

FIG. 9: Intranasal administration of Memogain leads to low amounts of liberated galantamine in plasma.

Figure 10:
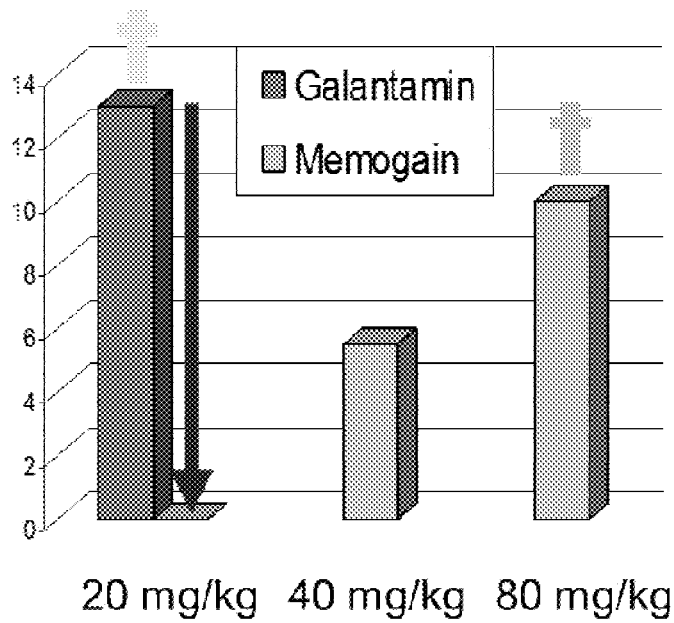

FIG. 10: Memogain produces fewer gastro-intestinal side effects than galantamine.

Figure 11:
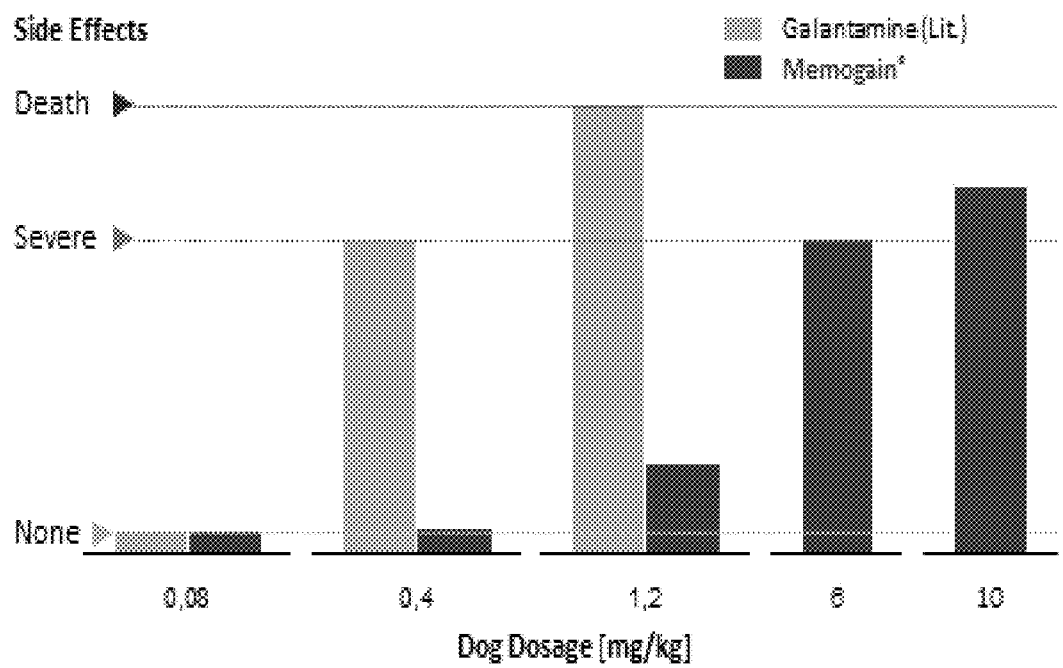

FIG. 11: Lower toxicity of Memogain is due to the lower steady-state plasma levels of galantamine resulting from enzymatic cleavage of the pro-drug.

Figure 12:
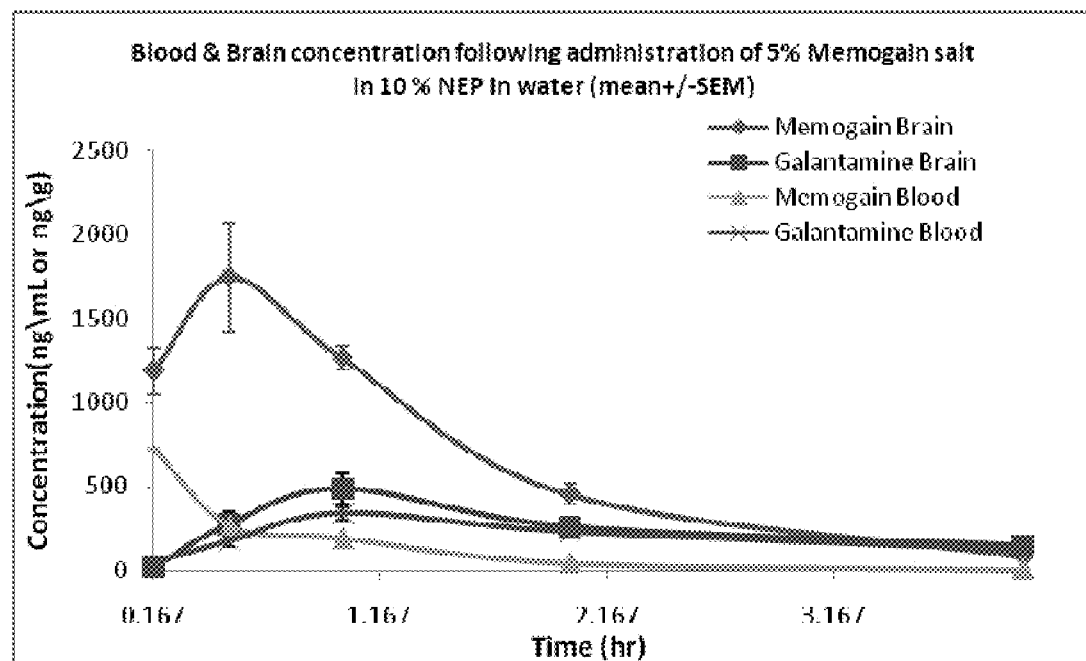

FIG. 12: The pharmacokinetic profiles of Memogain and galantamine in female Wistar rat after intra-nasal application of 5% Memogain salt in 10% NEP in water, 10 μL per nostril, a total of 20 μL containing 1 mg are shown below.

Figure 13:
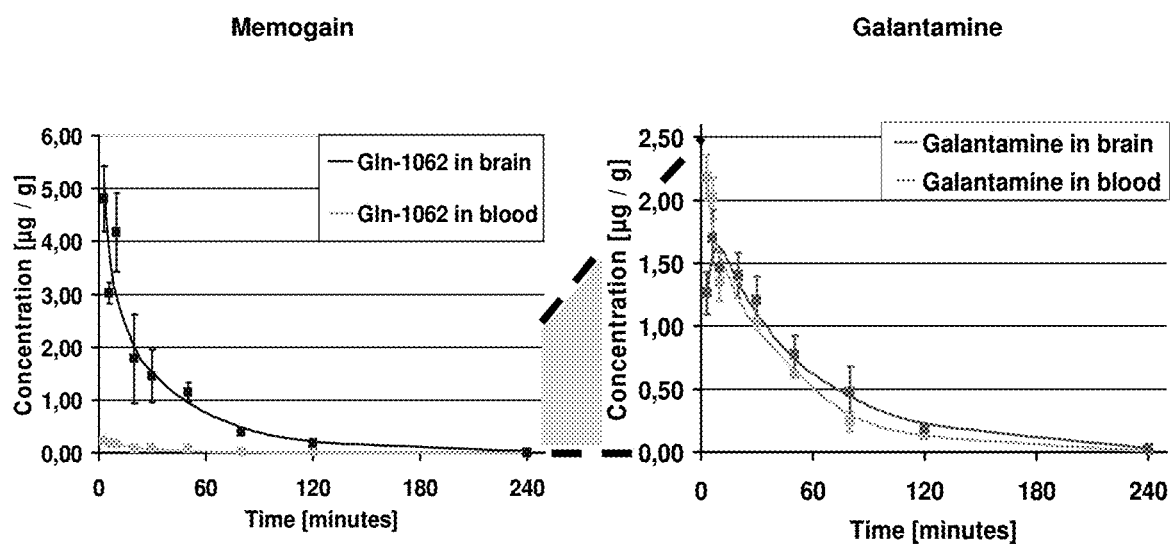

FIG. 13: Mice were injected with 3 mg/kg i.v. of either Memogain or galantamine. The data demonstrate that galantamine does not penetrate the brain well compared to Memogain.

Figure 14:
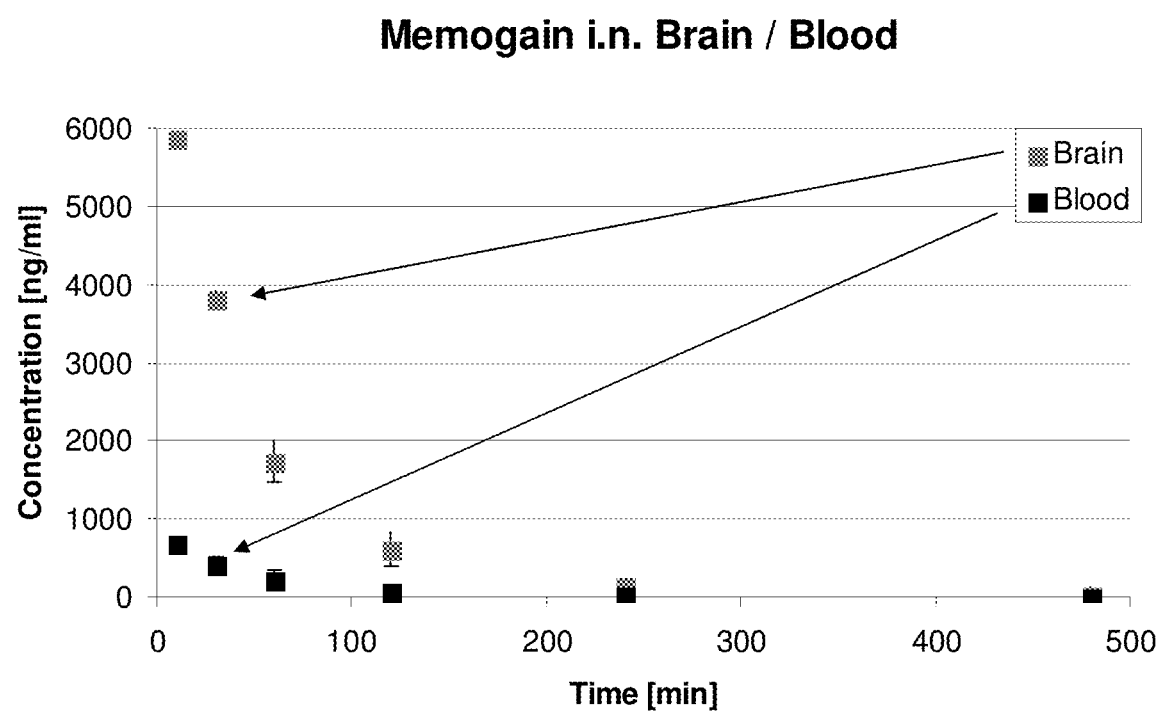

FIG. 14: Intranasal administration of Memogain in a Rat PK study. 5 mg/kg intranasal (i.n.) Memogain dosing was performed under GLP-like conditions.

EXAMPLES

The invention is further described by the following examples. The examples are intended to further describe the invention by way of practical example and do not represent a limiting description of the invention.

Example 1. High-Concentration Aqueous Salt Solutions and Organic Solvent Solutions of Pro-Drugs For one of the drugs considered herein, galantamine, intranasal formulations were previously developed on the basis of aqueous solutions of highly soluble salts (WO 2005/102275 A1; Leonhard A K et al. (2005) Development of a novel high-concentration galantamine formulation suitable for intranasal delivery. J Pharmaceut Sciences 94: 1736-1746; Leonard A K et al. (2007) In vitro formulation optimization of intranasal galantamine leading to enhanced bioavailability and reduced emetic response in vivo. Int J Pharmaceutics 335: 138-146).

While the reported galantamine salt formulations allowed administration of galantamine at similarly high doses as is recommended for oral administration of tablets, intranasal administration did not improve the brain/blood concentration ratio of galantamine, as the physicochemical properties of the drug and hence penetration through the BBB did not change by this approach. In contrast, when the same salt formulations are formed from the pro-drugs disclosed herein, a large increase in lipophilicity (log P) is achieved, concomitantly with much better penetration through the BBB. This can be seen in FIG. 1.

The combination of salt formation with prodrug properties, in particularly with regard to GLN 1062, shows a synergistic effect of improved absorption through the mucosal membrane and direct uptake to the brain, thereby enabling enhanced delivery to the site of action.

The blood-brain barrier penetration achieved by the various salts of the invention—in comparison to both the galantamine base compound, but also in comparison to oral administration of the derivatives themselves,—is increased in an unexpected and significant manner.

1.1. Salt of Memogain with Acetic Acid: (General Procedure A):

To the solution of Memogain (502 mg, 1.28 mmol in 2 ml 96% ethanol) acetic acid (463 mg, 7.71 mmol) was added and the resultant solution was stirred for some time and left overnight for salt formation resulting in the precipitation of the acetate salt. The yield was improved by addition of diethyl ether and the precipitate was filtered and washed with 96% ethanol. The precipitate was dried in a desiccator at r.t. at 40 mbar for 20 h. Results: colorless solid (Hygroscopic). Yield: 62%, m.p.: 89.3-91.2° C., HPLC>95%. Elemental analysis: Calcd. for $C_{24}H_{25}NO_4*1.5\ CH_3COOH$ C: 71.24, H: 6.46, N: 3.32 Found C: 71.36, H: 6.17, N: 3.43.

Several other crystal forms containing 1-2 molar equivalents of acetic acid were obtained in a similar manner by changing the relative amounts of Memogain and acid as well as the precipitation method.

1.2. Salt of Memogain with Lactic Acid: (General Procedure B):

To the solution of 2.5 g Memogain (6.4 mmol) in methanol (4 ml) a solution of 95% racemic lactic acid (7.85 mmol) in methanol (2 ml) was added at 40-50° C. and stirred for 20 min. The solvent was evaporated and the resulting residue was dried first using a rotavap for 2 hrs at 9 mbar and at 50-60° C. followed by overnight drying at 40 mbar at r.t. resulting in a solid light yellow foam that was highly hygroscopic. Yield: 98.92%, m.p.: 62.9-64.1° C., Elemental analysis: Calcd. for $C_{24}H_{25}NO_4*1.1\ C_3H_6O_3$ C: 66.84, H: 6.49, N: 2.86. Found: C: 66.69, H: 6.45, N: 2.80 HPLC purity>97%.

In a similar manner the corresponding salt with (+)-lactic acid was obtained: Calcd. for $C_{24}H_{25}NO_4*1.5\ C_3H_6O_3$ C: 65.01, H: 6.51, N: 2.66. Found: C: 64.91, H: 6.28, N: 2.70.

1.3. Salt of Memogain with Citric Acid:

Using general procedure B but dry ethanol as solvent the citrate was obtained in 91.0% yield as sticky solid that turned into a colorless solid after trituration using dry diethyl ether followed by high vacuum evaporation with m.p.: 117.5-119° C. Elemental analysis: Calcd for C: 73.64, H: 6.44, N: 3.58 Found C: 59.61, H: 5.93, N: 2.26. HPLC>97%

1.4. Salt of Memogain with Saccharic Acid (General Procedure C):

To a solution of Memogain (1120 mg) in 96% ethanol (4 ml) was added a solution of saccharolactone (200-604 mg) in 96% ethanol (3 ml) at 600. The hot solution was immediately diluted with ethyl acetate resulting in the formation of a colorless precipitate that was filtered after cooling to 50 for 2 hrs, washed with ethyl acetate and dried at 40 mbar for 20 hrs at r.t. to give a 83.7% yield of the saccharic acid salt as colorless solid with m.p.: 132-134° C. and HPLC-purity of >97%. Elemental analysis: Calcd. for $C_{24}H_{25}NO_4*C_6H_{10}O_8O$ C: 59.89, H: 5.86, N: 2.33. Found: C: 60.10, H: 5.61, N: 2.37. The lactone of saccharic acid is hydrolyzed with water present under these conditions resulting in the salt described.

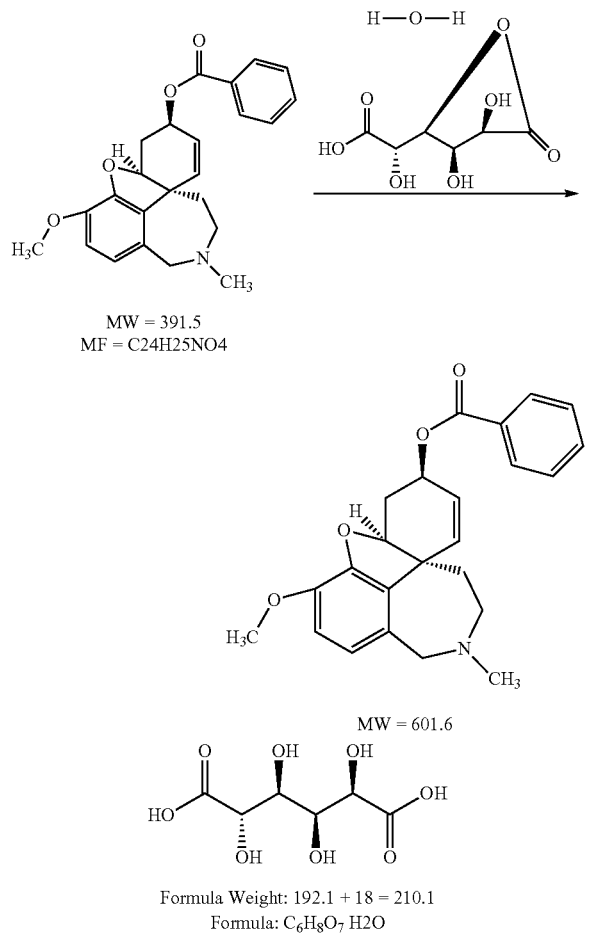

MW = 391.5
MF = C24H25NO4

MW = 601.6

Formula Weight: 192.1 + 18 = 210.1
Formula: $C_6H_8O_7$ H2O 1.5. Salt of Memogain with Gluconic Acid:

Following in general procedure C starting from Memogain (150 mg, 0.38 mmol) but using dioxane as solvent and a solution of D-gluconic acid delta-lactone (68.2 mg, 0.38 mmol) in dioxane containing water (13 mg, 0.76 mmol) and stirring at 50-60° C. for 30 min. until a clear solution was obtained followed by addition of dry diethyl ether (10 ml) to the cooled solution resulted in a colorless precipitate that was filtered, washed with diethyl ether and dried to obtain 170 mg (75.6%) of the salt as colorless, crystalline solid. m.p.: 159.3-159.4° C. HPLC purity>98% Elemental analysis: Calcd. for $C_{24}H_{25}NO_4*1.5\ C_6H_{12}O_7$ C: 57.80, H: 6.32, N: 2.04. Found: C: 58.22, H: 5.98, N: 2.28. The powder diffraction diagram of this salt is shown in FIG. 1.

From a similar experiment on twice the scale but without adding diethyl ether for precipitation spontaneous crystals were formed on standing at r.t. for 3 days that were filtered, washed with dioxane and dried to obtain 145 mg (32%) of the 1:1 salt as colorless crystals with m.p. 173.3-173.4° C. Calcd. for $C_{24}H_{25}NO_4*C_6H_{12}O_7$ C: 61.32, H: 6.35, N: 2.38. Found: C: 61.65, H: 6.27, N: 2.64. Microtitration of this salt verified the stochiometry calculated from the elemental analysis.

Under similar conditions but prolonged drying other salt-forms containing 0-2 equival. of water in the crystal were obtained. It is known that D-gluconic acid delta-lactone is hydrolyzed to gluconic acid by water.

In an alternative procedure ethanol was used as a solvent. Thus Memogain (9.4 g, 24 mmol) in 96% ethanol) was added to a solution of D-gluconic acid delta-lactone (6416 mg, 36 mmol) in 96% ethanol (10 ml) and heated to 50-60° C. for 30 min. until a clear solution was obtained that was kept at r.t. for 2 days with the formation of a colorless precipitate that was filtered, washed with dry ethanol (2×20 ml) and isopropanol (60 lm) and dried at 40 mbar at r.t. for 20 hr to obtain 7.91 g (84.2%) of the product as colorless crystalline solid m.p.: 122-126° C., HPLC purity>98%. Elemental analysis: Calcd. for $C_{24}H_{25}NO_4*C_6H_{12}O_7*H_2O$ C: 59.50, H: 6.49, N: 2.31. Found: C: 59.60, H: 6.59, N: 2.32.

This salt was used to obtain the adsorption/desorption isotherm of water (FIG. 2) as well as the weight loss on heating (FIG. 3). Furthermore by differential scanning calorimetry (DSC) of the wet cake of Memogain gluconate it was determined, that drying takes place between 53 and 87° C. and melting around 123° C. (FIG. 4). The powder diffraction diagram of this salt is shown in FIG. 5

$^{1H}$NMR (200 MHz, D2O): δ 7.35-7.46 (d, 2H), 7.09-6.94 (t, 1H), 6.92-6.80 (t, 2H), 6.59-6.36 (m, 2H), 6.14-6.00 (d, 1H), 5.85-5.72 (m, 1H), 5.16-5.07 (s, 1H), 4.48-4.31 (m, 4H), 4.13-3.84 (m, 5H), 3.73-3.53 (m, 6H), 3.53-3.39 (m, 5H), 2.76-2.58 (s, 3H) 2.39-2.21 (d, 1H), 2.06-1.69 (m, 3H)

$^{13C}$NMR (50 MHz, D2O): δ 178.39 (s, 1C), 167.03 (s. 1C), 146.09 (s, 1C), 145.11 (s, 1C), 133.09 (s, 1C), 131.57 (s, 1C), 129.26 (s, 1C), 128.04 (s, 1C), 123.75 (s, 1C), 123.40 (s, 1C), 119.02 (s, 1C), 118.74 (s, 1C) 118.67 (s, 1C), 112.05 (s, 1C), 85.82 (s, 1C), 73.93 (s, 1C), 73.52 (s, 1C), 72.46 (s, 1C), 71.07 (s, 1C), 70.81 (s, 1C), 64.23 (s, 1C), 62.54 (s, 1C), 58.51 (s, 1C), 55.52 (s, 1C), 53.98 (s, 1C), 46.50 (s, 1C), 40.96 (s, 1C) 40.82 (s, 1C), 32.07 (s, 1C), 26.83 (s, 1C).

Using the general procedures A, B and C the following salts were prepared on a 0.5 to 10 mmol scale in a similar manner and un-optimized yields of 42-91% were obtained. For those salts that were obtained in a crystalline state the melting points are indicated. Salts that showed solubility in water higher than 10% or even 20% were investigated further.

In addition to this list, pharmaceutically acceptable salts as described in table 1 of the book Pharmaceutical Salts, Properties, Selection and Uses, Stahl, P. H. and Wermuth, C. G., eds., VHCA Verlag 2002, can be used.

1.6. Solubility Test 10 mg of the corresponding salt and 100 microliters of water were sonicated for 5 min at r.t. The resulting solution or suspension was centrifuged for 3 min. and filtered using a filter tip. 10 microliters of the filtrate was transferred in a volumetric flask and diluted to 10.0 ml with water to obtain the sample solution. 20 microliters of this sample solution was injected for HPLC and the amount of Memogain quantified using a Merck Chromolith RP18 column and a gradient of 5% to 60% acetonitrile and water, both solvents containing 0.1% formic acid, injection volume: 20 microliters.

The Memogain salts of acetic acid, maleic acid, lactic acid (lactate salt), citric acid, saccharic acid (saccharate salt) and gluconic acid (gluconate salt) all showed solubility at above 10% in water.

The lactate, gluconate, maleate and saccharate salts of Memogain showed solubility above 10% weight per volume (w/v), sometimes forming meta-stable salts at 20% concentration in solution. The gluconate salt showed solubility at 40% weight per volume (w/v) and the saccharate salt at 70% weight per volume (w/v).

TABLE 3

Additional Memogain Salts

| Acid | m.p.(° C.) |
|---|---|
| Ascorbic acid | 110-131 (decomp.) |
| Arabic acid | 213 (decomp.) |
| Adipic acid | |
| DL-Mandelic acid | |
| D-Glucoheptono-1,4-lactone | 147 (decomp.) |
| Formic acid | 146-147 |
| Fumaric acid | |
| Galactaric acid | 143-144 |
| D-(+)-Galacturonic acid | 148-151 |
| Glucuronic acid | 145-146 |
| Glycolic acid | 97-103 |
| Hydrobromic acid | 221-222 |
| Hydroxy citric acid | |
| Hydrochloric acid | |
| Isethionic acid | 191-195 |
| Maleic acid | |
| L-(-)-Malic acid | 107-108 |
| Malonic acid | |
| Nicotinic acid | 117-118 |
| Phosphoric acid | |
| Succinic acid | |
| Sulfuric acid | 172-173 |
| L-(+)-Tartaric acid | 185-186 |
| D-(-)tartaric acid | 212-213 |
| Meso tartaric acid | 107-109 |

Particularly preferred are quaternary nitrogen salts (otherwise termed quaternary ammonium salts) of acetic acid, maleic acid, lactic acid (lactate salt), citric acid, saccharic acid (saccharate salt) and gluconic acid (gluconate salt).

These acids form salts with Memogain and other galantamine pro-drug nitrogen bases having solubility of up to 70% at neutral pH in water. While high-concentration of the gluconate salt in aqueous solution is metastable and is later converted to less soluble stable salt forms, the fully dissolved homogenous solutions can be recovered by warming the aqueous mixtures to >50° C. until precipitations have disappeared. These metastable homogenous solutions remain stable for hours and days, provided that precautions are taken to reduce or avoid precipitation seeding. Appropriate documentation of the dissolution procedure to form such metastable (hypercritical) solutions renders these solutions suitable drug product formulations for use by patients and medical personal. A short warming, for example for 5 minutes by hand, before administration allows optimal administration of such metastable solutions.

As sustained release aqueous formulations of the pro-drugs discussed here, we have dissolved in water a powder of the natural biopolymer chitosan, and mixed it with Memogain base or hydrogen salt so as to achieve formulations for intranasal delivery of 5% (w/v) or more (Illium L et al. (2002). Intranasal delivery of morphine. J Pharmacol Exp Therap 301: 391-400). The method of application described in Illium et al is also suitable for use with the chemical substances of the present invention.

Sustained release formulations of Memogain salts comprising chitosan also proved effective when applied in solid form in oral sublingual or buccal administration, and showed unexpectedly fast initial absorption with long release times.

The preferred salts of the present invention represent preferred embodiments that exhibit unexpectedly surprising and advantageous effects in comparison to what was disclosed in the prior art or what could have been expected by a skilled person in light of the prior art. The solubility of the particular preferred salts is unexpectedly good, allowing a higher concentration of medicament in the pharmaceutical composition (i.e. in the form of a solution in a particularly preferred embodiment for intranasal administration, but also buccal or sub-lingual application). This is of great importance in light of the requirements mentioned above for compounds that are suitable for intranasal, sublingual or buccal administration. Due to the limited size of the nasal cavity the required concentration of the active substance in solution is high. This means that salts needed to be found, which could be very soluble and therefore provided at a high concentration. This is surprisingly the case for the salts mentioned herein, preferably for acetic acid (acetate salt), lactic acid (lactate salt), citric acid, saccharic acid (saccharate salt) and gluconic acid (gluconate salt).

Example 2. Emulsions and Selfmicroemulsifying Drug Delivery Systems (SMEDDs)

Emulsions and SMEDDs are established means of brain delivery systems (Botner S, Sintov A C (2011) Intranasal delivery of two benzodiazepines, Midazolam and Diazepam, by a microemulsion system. Pharmacol Pharmacie 2:180-188). In the present application they were produced by mixing the pro-drug under investigation, as nitrogen base or as hydrogen salt, with various organic solvents or by mixing with suitable surfactants, oils and co-surfactants (all recognized as safe; GRAS) under stirring and/or ultrasound until a clear solution was achieved. In particular, we avoided using alcohols or other irritant chemicals in the formulations so as to avoid any irritability of the nasal or buccal mucosa. Typical components of such microemulsions were Labrasol, N-ethyl-2-pyrrolidone (NEP), glyceryl oleate, PEG, propylene glycol, Transcutol, and suitable oils, such as palmitate. We achieved drug solubilities of the order of 10% (w/w), or more, with a maximal water solubilization capacity of approx. 50% (the lower the water content, the higher oil concentrations could be achieved, and the higher the solubility of nitrogen base). The highest solubilities of pro-drug nitrogen bases or salts were obtained at water concentrations around 20% in the microemulsions.

Preferred embodiments of the self-microemulsifying drug delivery (SMEDD) formulation, preferably for Memogain maleate, relate to the following:

Used Materials:
Memogain maleate (No. 022563-A-1-1, GALANTOS Pharma GmbH, Germany)
Capmul MCM (Lot: 080726-7, BERENTZ—ABITEC CORP., USA)
(glyceryl caprylate/caprate; Pharm. Eur.)
PEG 300/400 (Lot: 1349048-41108320, FLUKA, Vienna, Austria)
(polyethyleneglycol; Pharm. Eur.)
Propyleneglycol (Lot: S44324-108, SIGMA, Vienna, Austria)
(propyleneglycol; Pharm. Eur)
Transcutol (Lot: 18703CE, SIGMA, Vienna, Austria)
(diethyleneglycolemonoethylether; Pharm. Eur.)
Preparation of a 10% Memogain maleate SMEDD formulation (1 L):
As the first step, 100 g of Memogain maleate are weighted into an appropriate steel tank.

In the following the solubilizers and fatty oils are added one after each other:

170 ml of Capmul MCM
500 ml PEG 300
220 ml Propyleneglycol
110 ml Transcutol

Finally the SMEDD formulation is treated with ultrasound until the mixture becomes a clear solution.

The Memogain base and salt emulsion and SMEDD formulations demonstrate reduced local irritation of the mucosal surface upon application. Furthermore, the bitter taste of the prodrug is effectively masked through the various lipid and PEG components and no analgesic effect on the transmucosal surface was evident.

Example 3. Micronized Powder Formulations and Nano-Suspensions of Pro-Drug Crystals Other suitable formulations for transmucosal delivery are pro-drug nano-crystals and polymeric micro-particles to which pro-drugs are adsorbed. In both cases, the more lipophilic pro-drug bases were used. The formulations were obtained by co-precipitation of polymer and pro-drug, by pearl milling and homogenization in water, or as nano-suspensions of pro-drugs that are lipid conjugates. Such methods are known to one skilled in the art and could be applied with the chemical substances and methods of administration of the present invention.

The micronized powder compositions of GLN 1062 or salts thereof enable fast absorption and a reduction in the bitter taste of the compound, compared to when applied as an aqueous solution.

Example 4. Memogain-Formulations

Solubility of Memogain
Free Base in Water: 26 µg/ml (66 µM)
Maleate in Water: 7.5 mg/ml (15 mM)
Maleate in 0.9% NaCl: 0.6 mg/ml (1.5 mM)
Free Base in Cyclodextrin-Vehicle[1]: 8.9 mg/ml (23 mM)
Maleate in Cyclodextrin-Vehicle): 21 mg/ml (41 mM)

[1] 15% (109 mM) Hydroxypropyl-β-cyclodextrin, 96 mM NaCl

TABLE 4

| | Formulations |
|---|---|
| Name | GEA1 |
| Type | Sublingual Tablet |
| API | Memogain maleate |
| API/Tablet | 1 mg |
| Tablet mass | 20 mg |
| Carrier | Lactose monohydrate |
| | Ethanol [1] |
| | Corn starch |
| | Povidon K30 (polyvinylpyrrolidone (PVP)) |
| | Magnesium stearate |
| | [1] removed during production |
| Name | GEA2 |
| Type | Sublingual Tablet |
| API | Memogain maleate |
| API/Tablet | 2 mg |
| Tablet mass | 50 mg |
| Carrier | Mannitol |
| | Explotab (sodium starch glycolate) |
| | Croscarmellose |
| | Ascorbic acid Magnesium stearate |
| | Orange flavour |
| Name | Evonik 1 |
| Type | Multi-layered Pellets (ca. 1 mm) with digestive acid resistant coating |

TABLE 4-continued

| | Formulations |
|---|---|
| API | Memogain maleate |
| API-amount | 1% |
| Pellet core | Cellet 700 (MCC) |
| API-layer | Memogain maleate and Methocel E5 (HPMC) |
| Subcoating | Methocel E5 (HPMC) |
| Coating | Eudragit FS30D, Talc, Triethylcitrate |
| Layer thickness | Approx. 30 µm bei 15% Coating; |
| Eudragit: | also Pellets with 5% and 10% were manufactured. |
| Name | Evonik 2 |
| Type | Multi-layered Tablets (appr. 9 mg) with digestive acid resistant coating |
| API | Memogain maleate |
| API-amount | 2 mg |
| Pellet core | Memogain maleat, Avicel PH 102 (MCC), corn starch, Methocel E5 (HPMC), Magnesium stearate |
| Subcoating | Methocel E5 (HPMC) |
| Coating | Eudragit FS30D, Talc, Triethylcitrate |
| Layer thickness | appr. 90 µm bei 15% coating; |
| Eudragit: | also Pellets with 5% and 10% were manufactured. |

The sub-lingual tablets and multi-layered formulations of the present invention show surprisingly good adsorption properties, enabling quick uptake and reduced flavour bitterness, in addition to reduced analgesic effects in the mouth of the patient. The fast adsorption of chemical substance enables a reduced risk of swallowing; thereby ensuring the administration occurs transmucosally through the oral mucous membrane, avoiding unwanted degradation of the prodrug.

Example 5. Interaction with Carrier Substance and Eudragit (Poly(Meth)Acrylate)

Experiment 1: a small amount (0.1 mg) of Memogain maleate in 1 ml HBSS-Puffer, pH 7.4 was incubated with various carriers at 37° C. 2.5 h. The amount of free (not bound to the particle of the carrier substance) of Memogain was then measured by HPLC. Typical amounts of carrier substance were applied and shown in Table 5.

TABLE 5

| Nr. | Substance | mg carrier | Non-absorbed Memogain (% of control) |
|---|---|---|---|
| control | none | 0 | 100 |
| 1 | Lactose | 10 | 105 |
| 2 | MCC | 10 | 100 |
| 3 | HPMC | 1 | 105 |
| 4 | Corn starch | 5 | 100 |
| 5 | Eudragit L100 | 2 | 21 |
| 6 | Eudragit FS30D | 1.8 | 7 |
| 7 | Talc | 2 | 94 |
| 8 | Mg Stearate | 0.1 | 101 |
| 9 | Mg Stearate + Tw20 | 0.1 plus 0.1% Tw20 | 103 |
| 10 | Aerosil (SiO$_2$) | 1 | 89 |
| 11 | Emcompress (CaHPO$_4$) | 10 | 101 |
| 12 | Explotab | 2 | 99 |
| 13 | Triethylcitrat | 0.2 | 101 |

Result: Eudragit L100 and Eudragit FS30D adsorb Memogain.

Experiment 2: a fixed amount of Eudragit (0.5 mg/ml) was incubated with various amounts of Memogainmaleate for 2 h in a saline solution (HBSS). The amount of free (not bound to the particle of the carrier substance) of Memogain was then measured by HPLC. In parallel the solubility of the Eudragit amount alone in the salt solution was analysed.

Result: L100 is completely soluble in the provided concentration, FS30D forms a cloudy solution. FS30D binds to Memogain over the entire tested concentration range. As of 0.25 mg/ml Memogain forms a precipitate with L100, which can be re-solubilised by the addition of 6% Cycldodextrin (HPCD).

Example 6. In Vitro Studies of Permeation Behavior, Pre-Systemic Metabolism and Stability Permeation behavior of pro-drug formulations was tested using tissue samples of 3-4 cm$^2$ freshly excised porcine nasal or buccal mucosa inserted in an Ussing-type chamber displaying a permeation area of 0.64 cm$^2$ and a volume of 1 ml on both sides. The apical side of the tissue was facing the donor compartment. One ml of pre-warmed (37° C.) permeation medium was added to the donor and acceptor chamber. The temperature within the chambers was maintained at 37° C. throughout the entire experiment. After a pre-incubation time of 15 min the permeation medium in the donor chamber was substituted by a 1% solution of the pro-drug formulation under investigation. Every 30 min aliquots of 100 µl were withdrawn from the acceptor compartment and immediately replaced by 100 µl of fresh pre-warmed permeation medium over a time period of 180 min. The concentration of compounds in the collected aliquots was determined via HPLC. Corrections were made for previously removed samples. Apparent permeability coefficients (Papp) were calculated. Control samples were withdrawn from the donor compartment after 180 min and analyzed to investigate the stability of the compound in the formulation under investigation.

During the above described permeation experiments, 10 µl aliquots were withdrawn from the donor compartment at time points 0, 60, 120 and 180 min. These aliquots were analyzed by HPLC to determine the degree of pre-systemic metabolism over time.

Using these methods, aqueous solutions of pro-drug salts, and solutions of pro-drug bases in organic solvents, co-solvents and surfactants were tested as to their solubility, their permeation coefficient, and their pre-systemic metabolism and stability. The formulations further studied had solubilities of at least 10% (m/v), and permeation coefficients of pro-drugs of Papp>1·10$^{-6}$ cm/s. Within the time periods tested, there was no significant pre-systemic metabolism of pro-drugs in both porcine mucosa preparations.

Example 7. Pharmacokinetics

The pharmacokinetics of pro-drugs and parent drugs after transmucosal delivery in the nasal or buccal cavity were tested in Wistar rats. These data confirmed rapid (within minutes) uptake into blood and brain of the pro-drugs under investigation, bioavailabilites in the brain of pro-drugs similar to those produced by intravenous injections, and much higher BBRC, as compared to oral delivery as tablet of the related parent drug.

Because redistribution of parent drug via BBB to the circulation, after enzymatic production from pro-drug in the brain, is very fast indeed, pharmacokinetic studies do not suffice to exactly determine the momentary concentrations of parent drug in the brain. We therefore used pharmacodynamics studies to determine the effective concentrations of parent drug in suitable experimental conditions, such as the reversal of scopolamine-induced temporary amnesia in the T-maze cognitive paradigm studied in mice. These studies confirmed that several fold higher (up to 20 fold) BBRC of parent drug (and related effectiveness in cognitive enhancement) can be achieved by transmucosal delivery of pro-drug formulations via the nasal or buccal cavity.

Experiments directly comparing potency and reduced GI side effects of Memogain between oral and transmucosal (nasal) administration also demonstrate that intranasally administered Memogain exhibits surprisingly beneficial properties in comparison to orally administered Memogain.

Pharmacokinetic studies were carried out using intranasal and sublingual administration of the Memogain maleate salt.

Intranasal Report:

This experimental plan describes the blood and brain pharmacokinetic profiles of the pro-galantamine Memogain maleate and galantamine in female wistar rat following intra-nasal application of the Memogain maleate and galantamine Hydrobromide in various formulations.

a. 5% galantamine in water, 1 µL per nostril, a total of 2 µL containing 1 mg 5%
b. Memogain salt in 10% NEP in water, 10 µL per nostril, a total of 20 µL containing 1 mg
c. 5% Memogain salt in an emulsion, 10 µL per nostril, a total of 20 µL containing 1 mg
d. 20% Memogain salt in an emulsion, 10 µL per nostril, a total of 20 µL containing 4 mg
e. Intravenous administration of Memogain salt at dose rate of 5 mg\kg (previously carried out as control)

Sublingual Report:

This experimental plan describes the blood and brain pharmacokinetic profiles of the pro-galantamine Memogain maleate and galantamine in female wistar rat following sub-lingual application of the Memogain maleate and galantamine Hydrobromide in various formulations.

a. 5% galantamine in water, 20 µL under tongue containing 1 mg
b. 5% Memogain salt in 10% NEP in water, 20 µL under tongue containing 1 mg
c. 5% Memogain salt in an emulsion, 20 µL under tongue containing 1 mg
d. 20% Memogain salt in an emulsion, 20 µL under tongue containing 4 mg
e. intravenous administration of Memogain salt at dose rate of 5 mg\kg as control Both the intranasal and sublingual studies show that beneficial pharmacokinetic (PK) properties were observed with the maleate salt. Similar results are to be expected from the other preferred salts of the invention, when considering the additional experimentation described herein and in light of preliminary studies with nasal or buccal mucosa, which show good uptake across the mucosal membranes of all preferred salts of the invention. The PK data show that Memogain was detected in the brain for extended periods of time, and showed high brain to blood concentration ratios, indicating that very little of the applied prodrug is carried into the blood stream and subsequently degraded. Over time the levels of Memogain in the brain decrease, as levels of galantamine in the brain increase, which indicates cleavage of the prodrug to its active form in the brain of the subject. One example is shown for the intranasal experiment in FIG. 12, sample b.

The administration of the Memogain salt intranasally provides a very effective method of directing the prodrug specifically to the brain, where it is processed thereby releasing the active compound galantamine.

Memogain Gluconate:

Further tests were performed with Memogain gluconate. It has a much larger BBRC than galantamine (see FIG. 6).

The pharmacokinetics and brain-to-blood concentration ratios (BBRC) of several galantamine derivatives and their cleavage product galantamine were evaluated after intranasal administration in Swiss albino mice at a dose of 3 mg/kg. After extraction from brain and blood, the drug concentrations were determined by LC/MS/MS. For comparison, the BBRC for the parent drug galantamine was also determined. As demonstrated in the figure, the studied pro-galantamines all display larger BBRCs than galantamine, with a particularly large BBRC for Gln-1062

Memogain gluconate is highly water soluble and has no burning sensation to nose, or any taste or smell. Intranasal dosing can be done with simple spray-pump methods, although also many other methods can be used. As Memogain is a pharmacologically inactive precursor of galantamine and was administered intranasally as gluconate, no GI side effects were observed.

Example 8. Memogain Shows Improved Brain Penetration and Low Blood Levels Compared to Galantamine Data are shown in FIG. 13. Mice were injected with 3 mg/kg i.v. of either Memogain or galantamine. The data demonstrate clearly that galantamine does not distribute into the brain well (BBRC~1:1), whereas Memogain has a much higher BBRC (8:1).

Additional data are shown in FIG. 14 for i. n. administration. A Rat PK study was carried out with 5 mg/kg intranasal (i.n.) Memogain dosing performed under GLP-like conditions. The data demonstrate that Memogain has a much higher BBRC (10:1).

Example 9. Intranasal Memogain is More Potent than Galantamine

To test whether intranasal Memogain is in-vivo a more effective cognition enhancer than galantamine, the following cognition paradigm was applied. Mice were treated with scopolamine to induce acute amnesia and were then tested for performance in a T-maze, in the absence or presence of oral galantamine or intranasal Memogain (FIG. 7). Clearly, Memogain was more effective than galantamine in reversing the acutely induced amnesia. Mice were challenged with Scopolamine i.p. in a T-maze assay to induce disorientation/amnesia (set to 0% performance recovery). Co-application of galantamine (i.p.) or of Memogain® (i.n.) rescues orientation in the T-maze in a dose-dependent manner.

Example 10. First Pass Effect of Memogain

The first-pass effect of Gln-1062 was evaluated after intravenous and intraportal dosing of 3 mg/kg in Wistar rats (FIG. 8). Gln-1062 was observed to undergo first-pass effect by rapidly decreasing blood concentration levels independently of whether it was administered i.v. or i.n. In contrast, the concentration levels of galantamine liberated from Gln-1062 by enzymatic cleavage did not decrease similarly rapidly. Moreover, higher maximal concentration levels of Gln-1062 were observed in brain and blood following i.v administration as compared to intraportal administration. From these data, the first-pass effect was estimated to be between 35 and 45%.

When Gln-1062 was administered intranasally at the same dose, similarly high maximal concentration levels were observed in the brain as after i.v. administration, indicating that uptake into the brain was as efficient as after i.v. administration and with little impairment by a first-pass effect.

Example 11. Intranasal Administration of Memogain Leads to Low Amounts of Liberated Galantamine in Plasma The study was performed in dogs. A single dose of 4 mg/kg intranasal Memogain was administered and the plasma levels of Memogain and liberated galantamine were determined as a function of time after administration. As Memogain is preferentially partitioned into the brain, only a small fraction of the pro-drug appears in the blood. The levels of galantamine liberated from Memogain are much smaller, as galantamine is rapidly metabolized and excreted (FIG. 9). This leads to a much reduced likelihood of side effects, considering the small amounts of systemic galantamine present in the blood after i. n. administration.

The data from the dog experiments demonstrate:
Brain:Blood ratio of Memogain (@120 min post administration)=9
Brain:Blood ratio of galantamine (@120 min post administration)=1-1.5
Memogain in blood $t\frac{1}{2}$=90 min (conscious animals)
Galantamine $t\frac{1}{2}$=6 h (conscious animals)
Low blood levels of galantamine indicates fewer side effects
High brain concentrations of Memogain indicate release of galantamine from Memogain mainly in the brain.

Example 12. Memogain Produces Fewer Gastro-Intestinal Side Effects than Galantamine These studies were performed in ferrets that were dosed i.p. with either 20 mg/kg galantamine (maximal tolerated dose), or with 20, 40 and 80 mg/kg Memogain, respectively. At 20 mg/kg Memogain, no adverse effects were observed. From the dose dependency of adverse effects, at least 4 times lower toxicity in this animal model was observed for Memogain, as compared to galantamine (FIG. 10).

Similarly, much less adverse effects than observed with galantamine were seen in the Irwin assay, respiratory toxicity studies, both performed in rats, and in a cardiovascular toxicity study in dogs.

Example 13. Memogain is at Least 10 Times Safer than Galantamine

This study was performed in dogs, and both drugs were administered as intravenous bolus. The lower toxicity of Memogain is due to the much lower steady-state plasma levels of galantamine resulting from enzymatic cleavage of the pro-drug (FIG. 11).

Medical Benefits of Galantamine Pro-Drugs and their Formulations for Transmucosal Delivery to the Nasal and Buccal Cavity:

The key benefits are as follows:
1. Higher bioavailability and higher effectiveness in the target organ
2. Lower levels of peripheral side effects
3. Pharmacokinetics can be adjusted to medical needs (sustained delivery)
4. Dosing not limited by GI adverse effects
5. Faster and stronger onset of medical benefit
6. Up-titration of dose (to enhance compliance) not needed 7. Immediate administration of efficacious doses
8. Improved patient compliance Higher bioavailability in the brain and higher effectiveness as a cognition enhancer was demonstrated by pharmacodynamics studies using suitable cognition paradigms in animal models of cognitive impairment. Dramatically lowered incidences of gastro-intestinal adverse effects, i.e. retching and emesis, were shown for intranasal delivery of Memogain in comparison to oral administration of identical doses of Memogain or galantamine. For intranasal delivery of the pro-galantamine Memogain, even at very high doses, GI-related side effects had practically disappeared, as the combined result of better brain penetration of the lipophilic pro-drug and avoidance of the gastro-intestinal tract during drug delivery.

In summary, the oral administration of Memogain and galantamine provide comparable BBB-penetration due to the rapid cleavage of Memogain (to galantamine) post-administration. The Memogain salts provide no noticeable enhanced effect when administered orally at the same concentration.

Intravenous administration (i. v.) of Memogain compared to galantamine demonstrates a vastly improved BBB-penetration for Memogain due to its more hydrophobic nature. The i. v. administration of galantamine provides only a very minor (if any) advantage in comparison to oral delivery of galantamine, as the active compound itself is relatively stable when compared to Memogain and is not susceptible to esterase cleavage.

Transmucosal administration (intranasal; i. n.) reveals unexpected enhanced effects with respect to Memogain, and particularly the salts of Memogain. The i. n. administration of the salts of Memogain show further improved BBB-penetration.

Brain penetration of galantamine is not enhanced by i. n. administration of galantamine, as the hydrophilic nature of the molecule prohibits effective penetration regardless of administration route. The i. n. administration of galantamine may avoid some common side effects (Leonard et al (2007)) of galantamine by avoiding administration through the digestive tract. The efficacy as cognition enhancer of the molecule is however not enhanced due to the remaining poor BBRC.

What is claimed is:

1. A method of treating a subject for a brain disease associated with cognitive impairment, comprising administering to a subject a chemical substance according to GLN 1062 or salt thereof:

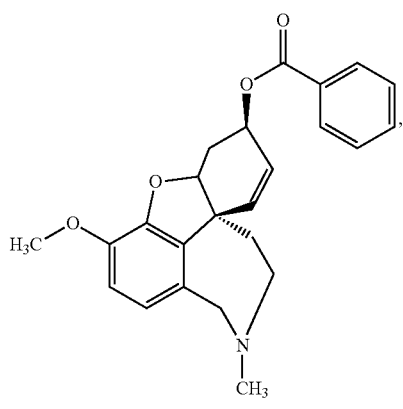

GLN-1062 wherein said treatment comprises sublingual administration of a therapeutically effective amount of GLN 1062 or salt thereof in the oral cavity of the subject.

2. The method according to claim 1, wherein GLN1062 is administered as a salt.

3. The method according to claim 1, wherein the salt comprises stoichiometric and/or non-stoichiometric salts and/or hydrates of GLN 1062, whereby the salt is described as: GLN 1062.n HX.m H2O:

whereby n, m=0-5 and n and m can be the same or different, and HX=an acid.

4. The method according to claim 2, wherein the GLN1062 salt is a gluconate salt.

5. The method according to claim 2, wherein the GLN1062 salt is a saccharate salt.

6. The method according to claim 2, wherein the GLN1062 salt is a maleate salt.

7. The method according to claim 2, wherein the GLN1062 salt is a lactate salt.

8. The method according to claim 2, wherein the GLN1062 salt has a solubility in water of at least 10% weight per volume (w/v).

9. The method according to claim 1, wherein GLN1062 or salt thereof is administered at a dosage of 1 to 100 mg one to three times daily.

10. The method according to claim 1, wherein GLN1062 or salt thereof is administered at a dosage of 2 to 40 mg twice daily.

11. The method according to claim 1, wherein the sublingual administration is carried out by administering a therapeutically effective amount of GLN1062 or salt thereof under the tongue by placing a sub-lingual tablet, one or more drops of a solution, or an amount of particulate in the form of freeze-dried powder or emulsion underneath the tongue and/or by spraying the underside of the tongue with a preselected volume of a liquid composition comprising the chemical substance.

12. The method according to claim 11, wherein the sublingual tablet comprises:

lactose monohydrate, corn starch, polyvinylpyrrolidone (PVP) and/or magnesium stearate, and optionally with a flavouring agent, or mannitol, sodium starch glycolate, croscarmellose, ascorbic acid and/or magnesium stearate, optionally with a flavouring agent.

13. The method according to claim 1, wherein the brain disease to be treated is selected from the group consisting of Alzheimer's Disease, Parkinson's disease, dementia, schizophrenia, epilepsy, stroke, poliomyelitis, neuritis, myopathy, oxygen and nutrient deficiencies in the brain after hypoxia, anoxia, asphyxia, cardiac arrest, chronic fatigue syndrome, poisoning, anaesthesia, spinal cord disorders, central inflammatory disorders, postoperative delirium, subsyndronal postoperative delirium, neuropathic pain, abuse of alcohol or drugs, addictive alcohol craving, nicotine craving, and effects of radiotherapy.

* * * * *